(12) United States Patent
Hung et al.

(10) Patent No.: US 6,413,228 B1
(45) Date of Patent: Jul. 2, 2002

(54) DEVICES, METHODS AND SYSTEMS FOR COLLECTING MATERIAL FROM A BREAST DUCT

(75) Inventors: David Hung, Belmont; Christopher G. M. Ken, San Mateo; Xuanmin He, Palo Alto; Phillip M. Olsen, Mountain View; Julian Nikolchev, Portola Valley; Shawn O'Leary, San Jose; Pam Sayavong, Newark, all of CA (US)

(73) Assignee: Pro Duct Health, Inc., Menlo Park, CA (US)

( * ) Notice: Subject to any disclaimer, the term of this patent is extended or adjusted under 35 U.S.C. 154(b) by 0 days.

(21) Appl. No.: 09/473,510

(22) Filed: Dec. 28, 1999

Related U.S. Application Data

(60) Provisional application No. 60/114,048, filed on Dec. 28, 1998, provisional application No. 60/134,613, filed on May 18, 1999, provisional application No. 60/143,359, filed on Jul. 12, 1999, and provisional application No. 60/170,997, filed on Dec. 14, 1999.

(51) Int. Cl.[7] .............................. A61B 10/00; A61B 5/00
(52) U.S. Cl. ....................... 600/562; 600/573; 604/28; 435/7.23
(58) Field of Search ................................ 600/562, 573, 600/576, 581; 435/7.21, 7.23; 604/28, 30, 35, 104; 119/14.19

(56) References Cited

U.S. PATENT DOCUMENTS

| | | | | |
|---|---|---|---|---|
| 3,527,203 A | * | 9/1970 | Gravlee ...................... | 600/563 |
| 3,608,540 A | | 9/1971 | Sartorius .................... | 600/563 |
| 3,786,801 A | | 1/1974 | Sartorius .................... | 600/573 |
| 3,792,703 A | | 2/1974 | Moorehead ................. | 604/158 |
| 3,821,956 A | | 7/1974 | Gordhamer et al. ........ | 606/191 |

(List continued on next page.)

FOREIGN PATENT DOCUMENTS

| | | |
|---|---|---|
| EP | 448395 | 3/1991 |
| EP | 542246 | 5/1993 |
| EP | 630657 | 5/1994 |
| EP | 631791 | 6/1994 |
| EP | 643979 | 8/1994 |
| EP | 682954 | 3/1995 |
| EP | 729766 | 9/1996 |
| EP | 800842 | 10/1997 |

(List continued on next page.)

OTHER PUBLICATIONS

M. Cukierfajn, J.P. Cattor and F. De Loose, "Intragalactophoric Aspiration: Description Of A Cytologic Examination Complementary To Galactography And First Results Obtained", pp. 101–106, dated 1983.

Barsky, et al. "Pathologic analysis of breast duct endoscoped mastectomies" Proc Annual Meeting Am Assoc. Cancer Res 34, abstracts #67.

(List continued on next page.)

*Primary Examiner*—Eric F. Winakur
*Assistant Examiner*—Charles Marmor, II
(74) *Attorney, Agent, or Firm*—Banner & Witcoff, Ltd.

(57) ABSTRACT

The invention provides methods, devices and systems for collecting breast ductal fluid comprising cellular material and other useful markers for analysis. The methods typically comprise access of at least one breast duct and collecting materials from that duct separate from all other ducts in the breast. The devices comprise ductal access devices that provide the opportunity to collect fluid from a single duct separate from all the other ducts in the breast. The systems employ the methods and devices that used together provide systems for analysis of a breast condition in a patient specific to accessed breast ducts. The methods, devices and systems are particularly useful for indentification of breast precancer or cancer in patient.

101 Claims, 12 Drawing Sheets

U.S. PATENT DOCUMENTS

| | | | |
|---|---|---|---|
| 4,406,653 A | 9/1983 | Nunez | 604/103 |
| 4,543,087 A | 9/1985 | Sommercorn et al. | 604/43 |
| 4,553,957 A | 11/1985 | Williams et al. | 604/43 |
| 4,596,564 A | 6/1986 | Spetzler et al. | 604/541 |
| 4,613,329 A | 9/1986 | Bodicky | 604/158 |
| 4,652,255 A | 3/1987 | Martinez | 604/27 |
| 4,680,029 A | 7/1987 | Ranford et al. | 604/523 |
| 4,709,705 A | 12/1987 | Truglio | 604/563 |
| 4,739,768 A | 4/1988 | Engelson | 600/435 |
| 4,790,830 A | 12/1988 | Hamacher | 604/274 |
| 4,795,424 A | 1/1989 | Burner et al. | 604/30 |
| 4,878,903 A | 11/1989 | Mueller | 604/199 |
| 4,944,729 A | 7/1990 | Buckberg et al. | 604/164.02 |
| 4,957,484 A | 9/1990 | Murtfeldt | 604/540 |
| 5,176,647 A | 1/1993 | Knoepfler | 604/158 |
| 5,183,470 A | 2/1993 | Wettermann | 604/523 |
| 5,209,734 A | 5/1993 | Hurley et al. | 604/158 |
| 5,215,527 A | 6/1993 | Beck et al. | 604/164.09 |
| 5,221,255 A | 6/1993 | Mahurkar et al. | 604/43 |
| 5,234,416 A | 8/1993 | Macaulay et al. | 604/527 |
| 5,246,430 A | 9/1993 | Mac farlane | 604/523 |
| 5,279,551 A | 1/1994 | James | 604/44 |
| 5,300,022 A | 4/1994 | Klapper et al. | 604/35 |
| 5,333,609 A | 8/1994 | Bedingham et al. | 600/339 |
| 5,350,358 A | 9/1994 | Martin | 604/43 |
| 5,368,574 A | 11/1994 | Antonacci et al. | 604/167.02 |
| 5,451,208 A | 9/1995 | Goldrath | 604/515 |
| 5,456,674 A | 10/1995 | Bos et al. | 604/526 |
| 5,470,318 A | 11/1995 | Griffith, III et al. | 604/161 |
| 5,593,393 A | 1/1997 | Trudell et al. | 604/264 |
| 5,599,324 A | 2/1997 | McAlister et al. | 604/523 |
| 5,637,102 A | 6/1997 | Tolkoff et al. | 604/536 |
| 5,649,909 A | 7/1997 | Cornelius | 604/96.01 |
| 5,683,640 A | 11/1997 | Miller et al. | 264/255 |
| 5,702,365 A | 12/1997 | King | 604/105 |
| 5,704,925 A | 1/1998 | Otten et al. | 604/272 |
| 5,763,415 A | 6/1998 | Sukamar | 514/44 |
| 5,795,326 A | 8/1998 | Siman | 604/43 |
| 5,797,869 A | 8/1998 | Martin et al. | 604/43 |
| 5,797,872 A | 8/1998 | Ogata et al. | 604/500 |
| 5,798,266 A | 8/1998 | Quay et al. | 436/64 |
| 5,800,534 A | 9/1998 | Jeter et al. | 623/8 |
| 5,810,789 A | 9/1998 | Powers et al. | 604/523 |
| 5,810,867 A | 9/1998 | Zarbatany | 606/191 |
| 5,827,237 A | 10/1998 | Macoviak et al. | 604/246 |
| 5,843,023 A * | 12/1998 | Cecchi | 604/44 |
| 5,921,971 A * | 7/1999 | Agro et al. | 604/523 |
| 6,010,466 A * | 1/2000 | McGeorge | 601/14 |
| 6,099,485 A * | 8/2000 | Patterson | 600/585 |
| 6,168,779 B1 * | 1/2001 | Barsky et al. | 424/9.2 |
| 6,221,622 B1 * | 4/2001 | Love | 435/7.23 |

FOREIGN PATENT DOCUMENTS

| | | |
|---|---|---|
| JP | 58-46337 | 3/1983 |
| JP | 58-146356 | 8/1983 |
| JP | 61-268266 | 11/1986 |
| JP | 11-19102 | 5/1989 |
| JP | 2-80058 | 3/1990 |
| JP | 3-4232 | 1/1991 |
| JP | 3-36363 | 8/1991 |
| JP | 4-4730 | 2/1992 |
| JP | 4-226675 | 8/1992 |
| JP | 5-184664 | 7/1993 |
| JP | 61-24022 | 5/1994 |
| JP | 61-24023 | 5/1994 |
| JP | 6/277289 | 10/1994 |
| JP | 6-2777294 | 10/1994 |
| JP | 6-77709 | 11/1994 |
| JP | 7-33798 | 8/1995 |
| JP | 8-112354 | 5/1996 |
| JP | 9-99089 | 4/1997 |
| JP | 2531583 | 4/1997 |
| JP | 2631320 | 7/1997 |
| JP | 2681345 | 11/1997 |
| JP | 10-118189 | 5/1998 |
| JP | 6-154334 | 6/1999 |
| JP | 2-191466 | 7/1999 |
| JP | 3-264045 | 11/1999 |
| WO | WO 88/05669 | 8/1988 |
| WO | WO 89/09079 | 10/1989 |
| WO | WO 92/10971 | 7/1992 |
| WO | WO 94/02197 | 2/1994 |
| WO | WO 94/07549 | 4/1994 |
| WO | WO 94/12089 | 6/1994 |
| WO | WO 95/20983 | 8/1995 |
| WO | WO 97/05898 | 2/1997 |
| WO | WO 97/10015 | 3/1997 |
| WO | WO 97/31677 | 9/1997 |
| WO | WO 97/37699 | 10/1997 |
| WO | WO 97/44082 | 11/1997 |
| WO | WO 97/44084 | 11/1997 |
| WO | WO 97/47230 | 12/1997 |
| WO | WO 97/48435 | 12/1997 |
| WO | WO 98/39046 | 9/1998 |
| WO | WO 99/13917 | 3/1999 |
| WO | WO 99/55384 | 11/1999 |

OTHER PUBLICATIONS

"Breast Fluid cells help in early cancer detection" JAMA May 7, 1973 vol. 224, No. 6.

"Cancer detection techniques shown." Santa Barbara News Press Aug. 3, 1971.

Cassels, "New test may speed breast cancer detection." The Medical Post Mar. 20, 1973.

Ernster, et al. "Benign and malignant breast disease: initial study results of serum and breast fluid analyses of endogenous estrogens." JNCI vol. 79 No. 5.

Fabian et al. "Biomarker and cytologic abnormalities in women at high and low risk for breast cancer" J of Cellular Biochemistry 17G:153–160 (1993).

Falardeau, et al. "Selective galactophorectomy for mono–orificial nipple discharge without associated mass: technique and results." US National Library of Medicine AN=92143500 [abstract of article in French], 1991.

Feige, "Dynamic morpho–cyto–echography and the echographic galactoscopy endo–ductal sample. Intrinsic and extrinsic markets in detection of breast cancers" US National Library of Medicine AN=8904507.

"Finding asymptomatic breast cancer." Medical World News Jul. 23, 197.

Fryckberg, et al. "Ductal carcinoma in situ of the breast." Surgery, Gynecology & Obstetrics 10/93 vol. 177.

Goodson & King. "Discharges and secretions of the nipple." *The Breast, Comprehensive Management of Benign and Malignant Diseases* 2nd ed vol. 2. 1998.

Hou et al. "A simple method of duct cannulation and localization for galactography before excision in patients with nipple discharge" Radiology, (May 1995) 195 (2) 568–9.

"'PAP' Test for Breast Cancer" newspaper clipping regarding Dr. Sartorius.

Katamine et al. "Determination of cancer–associated antigens in body fluid secreted from nipple." Chemical Abstracts, vol. 114, No. 9, Mar. 4, 1991.

Leborgne, *The Breast in Roentegen Diagnosis*, Uruguay 1953.

Lewis. "Technique probes breast ducts for cancer cells." Biophotonics News May/Jun. 1997.

Lobsenz. "A new way to detect breast cancer early." Good House Keeping Jan. 1975.

Love & Barsky. Breast–duct endoscopy to study stages of cancerous breast disease. The Lancet vol. 348 Oct. 10, 1996 pp 997–999.

Makita et al. "Duct endoscopy and endoscopic biopsy in the evaluation of nipple discharge." Breast Cancer Research and Treatment 18: 179–188 1991.

Masood. "The missing link: a 'pap smear' for early breast cancer detection and prevention." The Breast Journal, vol. 5 No. 1, 1999 pp. 1–2.

Naran et al. "Cytologic diagnosis of papillary carcinoma of the breast in needle aspirates" Diagnostic Cytopathology, (Mar. 1988) 4 (1) 33–7.

Okazaki, et al. "Relationship between cytologic results and the extent of intraductal spread in nonpalpable breast cancers with nipple discharge" Tumor Res. 31, 89–97 (1996).

Okazaki et al, "Fiber optic ductoscopy of the breast" Jpn J Clin Oncol 1991 21(3):188–193.

Okazaki et al. "Diagnosis of nonpalpable breast cancer by ductoscopy: comparison of imaging and histological findings." Nyugan no Rinsho[clinical breast cancer] 4(4):587–594(Dec. 1989).

Osborne. "Galactography with contrast and dye." Australian Radialogy vol. 23, No. 3 8/89.

Papanicolaou et al. "Exfoliative cytology of the human mammary gland and its value in the diagnosis of cancer and other diseases of the breast." Cancer Mar.–Apr. 1958, 11(2): 377–409.

Petrakis & King. "Genetic markers and cancer epidemiology." Cancer April supp 1977 vol. 39 pp 1861–1866.

Sartorius et al. "Contrast ductography for the recognition and localization of benign and malignant breast lesions: an improved technique." Breast Cancer New York Wiley pp. 281–300, 1977.

Sartorius, "Cytologic evaluation of breast fluid in the detection of breast disease" J Nat'l Cancer Inst vol. 59 No. 4 Oct. 1977 pp. 1073–1080.

Sartorius, "Fluid Cytology and Contrast Ductography".

Sauter et al, "Nipple aspirate fluid: a promising non–invasive method to identify cellular markers of breast cancer risk" 1997 British J. Cancer 76(4):494–501.

Strah & Love. "The in situ carcinomas of the breast." JAMWA vol. 47 No. 5 Sep./Oct. 1992.

Sukumar & McKenzie, "Breast cancer prevention strategies for the twenty first century" Molecular Medicine today 11/96.

Tabar et al. "Galactography: the diagnostic procedure of choice for nipple discharge." Radiology 149:31–38 Oct. 1983.

Walters et al. "A comparison of the dual lumen and coaxial catheters for temporary hemodialysis." Int. J. Artif Organs 1997 Apr: 20(4):208–12.

Weaver et al. "Management of postoperative lymphatic leaks by use of isosulphan blue '31" J Vascular Surgery, (1991) 14/4 (566–567).

Wrensch, et al. "Breast cancer risk associated with abnormal cytology in nipple aspirates of breast fluid and prior history of breast biopsy." Am J. of Epidemiology vol. 137 No. 8 1993.

Wrensch et al. "Factors associated with obtaining nipple aspirate fluid:analysis of 1428 women and literature review" Breast Cancer Research and Treatment 15:39–51, 1990.

Zippin & Petrakis, "Identification of high risk groups in breast cancer." Cancer vol. 28 pp 1381–1387 Dec. 1971.

"Ranfac product materials" updated Jun. 1998.

* cited by examiner

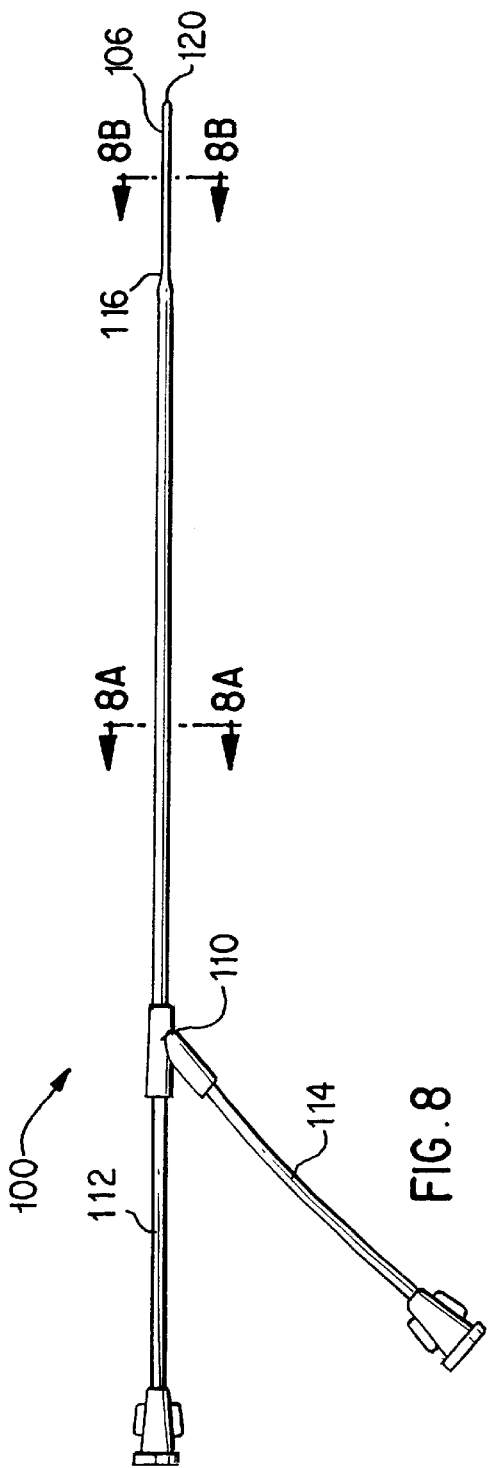
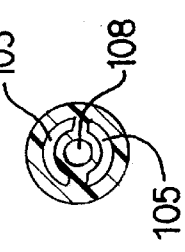
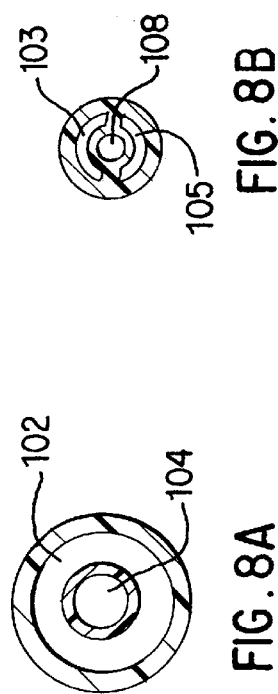
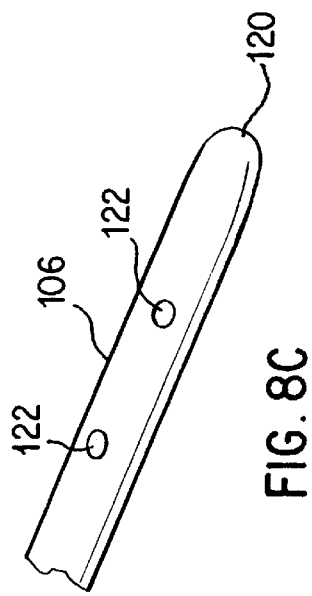
FIG. 8
FIG. 8A
FIG. 8B
FIG. 8C

DEVICES, METHODS AND SYSTEMS FOR COLLECTING MATERIAL FROM A BREAST DUCT

CROSS-REFERENCES TO RELATED APPLICATIONS

This application claims the benefit of each of the following provisional applications under 37 CFR §1.78: Ser. No. 60/114,048, filed on Dec. 28, 1998; Ser. No. 60/134,613, filed on May 18, 1999; Ser. No. 60/143,476, filed on Jul. 12, 1999; Ser. No. 60/143,359, filed on Jul. 12, 1999; and Ser. No. 60/170,997, filed on Dec. 14, 1999. The full disclosures of each these applications are incorporated herein by reference.

BACKGROUND OF THE INVENTION

1. Field of the Invention

The field of this invention is devices, methods and systems for collecting breast duct fluid from humans.

2. Description of the Background Art

For several decades significant members of the medical community dedicated to studying breast cancer have believed and shown that the cytological analysis of cells retrieved from nipple discharge from the breast milk ducts can provide valuable information leading to identifying patients at risk for breast cancer. Indeed Papanicolaou himself contributed to the genesis of such a possibility of a "Pap" smear for breast cancer by analyzing the cells contained in nipple discharge. See Papanicolaou et al, "Exfoliative Cytology of the Human Mammary Gland and Its Value in the Diagnosis of Cancer and Other Diseases of the Breast" Cancer (1958) March/April 377–409. See also Petrakis, "Physiological, biochemical, and cytological aspects of nipple aspirate fluid", *Breast Cancer Research and Treatment* 1986; 8:7–19; Petrakis, "Studies on the epidemiology and natural history of benign breast disease and breast cancer using nipple aspirate fluid" *Cancer Epidemiology, Biomarkers and Prevention* (January/February 1993) 2:3–10; Petrakis, "Nipple Aspirate Fluid in epidemiological studies of breast disease", *Epidemiologic Reviews* (1993) 15:188–195. More recently, markers have also been detected in nipple fluid. See Sauter et al, "Nipple aspirate fluid: a promising non-invasive method to identify cellular markers of breast cancer risk", *British Journal of Cancer* 76(4):494–501 (1997). The detection of CEA in fluids obtained by a nipple blot is described in Imayama et al. (1996) *Cancer* 78: 1229–1234.

Breast cancer is believed to originate in the lining of a single breast milk duct in the breast; and additionally human breasts are believed to contain from 6 to 8 of these ducts. See Sartorius, *JAMA* 224 (6): 823–827 (1973). Sartorious describes use of hair-like single lumen catheters that are inserted into breast ducts using an operating microscope and the ducts were flushed with saline solution as described in Cassels, D Mar. 20$^{th}$, 1973, *The Medical Post,* article entitled "New tests may speed breast cancer detection". Sartorius et al, Contrast ductography for recognition and localization of benign and malignant breast lesions: an improved technique. pp. 281–300. In: Logan W W, ed. Breast Carcinoma New York, Wiley, 1977. After the fluid was infused, the catheter was removed because it was too small to collect the fluid, the breast was squeezed and fluid that oozed onto the nipple surface was removed from the surface by a capillary tube. Similarly, Love and Barsky, "Breast-duct endoscopy to study stages of cancerous breast disease", *Lancet* 348(9033):997–999, 1996 describes cannulating breast ducts with a single lumen catheter and infusing a small amount of saline, removing the catheter and squeezing to collect the fluid that returns on the nipple surface. The use of a rigid 1.2 mm ductscope to identify intraductal papillomas in women with nipple discharge is described in Makita et al (1991) *Breast Cancer Res Treat* 18: 179–188. It would be advantageous to develop methods and devices to collect the ductal fluid from within the duct.

Galactography, or contrast ductography has for years located breast ducts based on spontaneous nipple discharge, infused the ducts (using cannulas for this purpose) with contrast dye solutions, and taken x-ray pictures to determine the source of the discharge within the duct. See generally, The Breast: Comprehensive Management of Benign and Malignant Breast Diseases, Bland and Copeland eds. W. B. Saunders Co. Philadelphia Pa. 1991 pages 61–67.

Method and kits for obtaining fluid and cellular material from breast ducts 09/067,661 filed Apr. 28, 1998, and its CIP 09/301,058 filed Apr. 28, 1999 describe and claim infusing a small amount of fluid into the duct and collecting the fluid using a catheter. It would be beneficial to optimize the cells and fluid collected from this procedure.

U.S. Ser. No. 60/143,359 filed Jul. 12, 1999 describes and claims a multilumen catheter for collection of infused fluid. U.S. Ser. No. 60/143,476 filed Jul. 12, 1999 describes and claims devices and methods for accessing the lactiferous sinus of a breast duct. U.S. Ser. No. 60/122,076 filed Mar. 1, 1999 describes devices, methods and kits for accessing more than one breast duct at a time for delivering and/or retrieving agents or materials to and from more than one breast duct at the same time. Related applications are U.S. Ser. Nos. 60/143,476 and 60/143,359 both filed Jul. 12, 1999 and U.S. Ser. No. 60/134,613 filed May 18, 1999, and U.S. Ser. No. 60/114,048 filed Dec. 28, 1998, all of which are herein incorporated by reference in their entirety.

Osmotic agents including sugars that are poorly absorbed, for example lactulose or sorbitol, have been used as laxatives. See THE MERCK MANUAL OF MEDICAL INFORMATION, Berkow, Beers and Fletcher Eds, 1997 Merck Res. Lab., Whitehouse Station, N.J. pp. 522–523. The osmotic agent mannitol is available as an injectable, 25% (Physicians Desk Reference 1996) for a variety of indications (e.g. renal insufficiency, congestive heart failure). A mixture of sorbitol and mannitol is compared to distilled water as an irrigant during transurethral prostatectomy in Sargin et al, (1997) *Int Urol Nephrol* 29:575–80. Intracranial pressure therapy has been provided by solutions of mannitol, sorbitol or glycerol as described in Treib et al, (1998) *Eur Neurol* 40: 212–219. Osmotherapy for increased intracranial pressure comparing the use of mannitol and glycerol is discussed in Biestro et al, (1997) *Acta Neurochir (Wien)* 138: 725–32; discussion 732–3. Mannitol therapy for renal conditions is described generally in Better et al, (1997) *Kidney Int* 52:886–894, and use of the osmotic diuretic mannitol for renal protection is analyzed in Visweswaran et al, (1997) *J Am Soc Nephrol* 8: 1028–33. Use of mannitol during cardiac catheterization is described in Willerson et al, (1975) *Circulation* 51:1095–1100 and Kurnick et al, (1991) *Am J Kidney Dis* 17:62–8. The osmotic effects of polyethylene glycol are discussed in Schiller et al, (1988) *Gastroenterology* 94: 933–41. Raffinose is used for peritoneal dialysis as described in Kohan et al (1998) *J Lab Clin Med* 131: 71–6.

Relevant Literature

Hou et al, "A simple method of Duct Cannulation and Localization for Galactography before Excision in Patients with Nipple Discharge." *Radiology* 1995; 195; 568–569 describes injecting a "small volume of sterile, water soluble contrast material . . . (0.5 ml–2.0 ml) . . . the catheter was taped on the breast or nipple . . . the contrast material was aspirated with the same syringe and gentle manual pressure was exerted on the breast to expel the opaque medium."

The use of a 0.4 mm flexible scope to investigate nipple discharge is described in Okazaki et al (1991) *Jpn J. Clin. Oncol.* 21:188–193 in which before the fiberoptic ductoscopy "a lacrimal cannula was inserted [into the duct] for ductal washing by infusing 0.2 to 0.5 ml physiological saline twice or three times, citing also Okazaki et al *Nyugan No Ringsho* 4:587–594 (1989) (in Japanese).

A company called Diagnostics, Inc. formed in 1968, produced devices to obtain breast ductal fluid for cytological evaluation. The devices included a hair-like single lumen breast duct catheter to infuse fluid into a breast duct and the procedure dictated that after removal of the catheter oozing fluid was collected from the nipple surface with a capillary tube. The devices were sold prior to May 28, 1976 for the purpose of collecting breast ductal fluid for cytological evaluation.

A lacrimal irrigating cannula is described in U.S. Pat. No. 5,593,393 to inventors Trudell and Prouty. The cannula is graduated and used for insertion, dilation, probing and irrigating of the lacrimal drainage system of the eye. Lacrimal probes have been used to access breast ducts as depicted in The Breast: Comprehensive Management of Benign and Malignant Diseases (1991) vol 2, Bland & Kirby eds. W. B. Saunders Co, Philadelphia, Pa. pp. 63, FIGS. 3–26.

Patents and applications that describe use of a fixed support wire or support generally to reinforce the catheter include PCT publication WO 97/44084, PCT publication WO 97/44082, U.S. Pat. No. 5,221,255, JP 6-154334 (unexamined patent publication), U.S. Pat. No. 3,792,703 to Moorehead, U.S. Pat. No. 4,596,564 to Spetzler et al, U.S. Pat. No. 5,209,734 to Hurley et al, U.S. Pat. No. 5,456,674 to Bos et al, PCT publication WO 97/31677, PCT publication WO 94/07549, PCT publication WO 94/02197, European patent application EP 630 657 A1, European patent application EP 800 842 A1, Japanese unexamined patent publications JP 4-226675, JP 6-277289, and JP 6-277294, Japanese examined patent publication JP 3-4232, and PCT publication WO 97/47230.

Patents and publications that describe use of a very small atraumatic tip include U.S. Pat. No. 4,652,255 to Martinez, U.S. Pat. No. 5,246,430 to MacFarlane, PCT publication WO 97/37699, PCT publication WO 97/10015, PCT publication WO 94/07549, European patent application EP 729 766 A1, European patent application EP 643 979 A1, Japanese examined utility model publication JP 4-4730, and Japanese examined patent publications JP 1-14794, JP 61-24022, and JP 61-24023.

Patents and publications that describe and claim fluid collection catheters having a narrow distal portion and a larger diameter proximal portion with a shoulder therebetween include PCT publication WO 97/44084, PCT publication WO 97/44082, U.S. Pat. No. 5,221,255 to Mahurkar, JP 2,519,873 (U.S. Pat. No. 5,470,318), U.S. Pat. No. 4,553,957 to Williams et al, U.S. Pat. No. 4,652,255 to Martinez, U.S. Pat. No. 4,709,705 to Truglio, U.S. Pat. No. 5,451,208 to Goldrath, U.S. Pat. No. 5,246,430 to MacFarlane, PCT publication WO 97/48435, PCT publication WO 97/31677, PCT publication WO 95/20983, PCT publication WO 94/02197, European patent application EP 682 954 A2, European patent application EP 631 791 A1, Japanese examined patent publication JP 4-45186, Japanese unexamined utility model publication 6-77709, PCT publication WO 98/39046, and WO 97/47230.

Other patents or publications related in the art include the following: JP 5-184664 assigned to Terumo Corp. describes a catheter with a distal tip formed by heating; JP 2.631,320 Moriuchi et al, assigned to Terumo Corp. showing vascular catheter with multiple axial wire supports extending the length of the catheter; JP 3-264045 to Sato, assignee Terumo Corp. has a central reinforcement wire extending the length of intravascular catheter body; JP 61-268266 (WO 89/09079) to Hurley et al, assignee Sumitomo Bakelite (abandoned) depicting another wire reinforcement but in a uterine catheter; JP 6-502314 to Hurley et al, assignee Brigham & Women's Hospital shows a spinal catheter with spinal wire reinforcement; JP 8-112354 to Takane depicts probe with isolate lumens and distal side ports; JP 5-237191 (EP 542246) to Pearsall, assignee Becton Dickinson shows rounded tips softer than the body of the catheter; JP 3-36363 (JP 4-516C) to Kamogawa, assignee Terumo Corp. is expired but has atraumatic tip with side ports and a single lumen; JP 2,531,583 to Onishi, assigned to Mitsubishi shows a catheter having a soft tip formed from polymer having a glass transition temperature at body temperature; JP 2,681, 345 to Inoue, assignee Kitasato Supply shows insemination device with syringe; JP 5-184664 to Takeoka, assignee Terumo Corp. shows a single lumen rounded tip catheter with side ports; JP 58-46337 (JP 59-2345) to Fujimoto depicts a slidable stop on rectal catheter having side ports; and JP 58-146356 to Harris depicts an intrauterine catheter with shoulder stop. Patents and publications that describe breast access for purposes other than lavage include U.S. Pat. No. 5,800,534 to Jeter et al.

SUMMARY OF THE INVENTION

According to the present invention, a method for obtaining cellular material from a human breast milk duct comprises introducing a wash fluid to the breast milk duct, using a volume of at least 2 ml that is present within the duct for a preselected time, and collecting at least a portion of the introduced wash fluid from within the duct, with the portion of wash fluid carrying the cellular material. The preselected time is preferably less than one second, but will usually be in the range from one second to one hour. The wash fluid is preferably introduced to a volume of at least 2 ml, often at least 5 ml, and typically in the range between 5 ml and 25 ml, prior to collecting any of the wash fluid from the duct. The wash fluid is preferably introduced to a single breast milk duct and collected from the same breast milk duct without mixing with materials from other breast milk ducts. The method may further comprise separating cellular material from the collected fluid. The method may still further comprise examining the separated cellular material. The cellular material usually includes a substance selected from the group consisting of whole cells, cellular debris, proteins, nucleic acids, polypeptides, glycoproteins, lipids, fats, glycoproteins, small organic molecules, metabolites, and macromolecules.

Another aspect of the invention comprises a method for obtaining cellular material from a human breast milk duct including introducing a ductal access device having at least one lumen into a duct, introducing a wash fluid through the access device lumen into the milk duct, providing a volume of at least 2 ml to be present within the duct for a preselected time, and then collecting at least a portion of the wash fluid from the duct through the lumen of the access device. The method preferably further comprises massaging and squeezing the breast tissue after introducing the wash fluid but prior to and/or during collecting a portion of the wash fluid. Introducing the ductal access device typically comprises positioning a distal end of the device distal to the ductal sphincter in the breast duct. The access device preferably includes only a single lumen that extends into the duct. The wash fluid is preferably introduced to a volume of at least 2 ml prior to collecting any of wash fluid from the duct. The preselected time can be less than one second, but will usually be in the range from one second to one hour. The wash fluid can be introduced to a single breast milk duct and collected from the same breast milk duct without mixing with materials from other breast milk ducts. The method may still further comprise separating cellular material from the collected fluid. The method may still further comprise examining the separated cellular material. The cellular material is usually a substance selected from the group consisting of whole cells, cellular debris, proteins, nucleic acids, polypeptides, glycoproteins, lipids, fats, glycoproteins, small organic molecules, metabolites, and macromolecules.

Another aspect of the invention is a method for obtaining cellular material from a human breast milk duct comprising introducing a wash fluid to the breast milk duct, providing that the wash fluid is present within the duct for a preselected time, and collecting at least a portion of the introduced wash fluid from within the duct, where the portion carries the cellular material; the wash fluid is introduced to a single breast milk duct and collected from the same breast milk duct without mixing with materials from other breast milk ducts. The volume of wash fluid can be at least 2 ml. The preselected time can be less than one second or can be in a range from one second to one hour. The method can further comprise separating cellular material from the collected fluid. The method can also further comprise examining the separated cellular material. The cellular material can be a substance selected from the group consisting of whole cells, cellular debris, nucleic acids, lipids, protein metabolites, small organic molecules, and macromolecules.

An aspect of the invention is another method for obtaining cellular material from a human breast milk duct comprising introducing a ductal access device having at least one lumen into a duct, introducing a wash fluid through the access device lumen into the milk duct, where the wash fluid is present within the duct for a preselected time, and collecting at least a portion of the wash fluid from the duct through the lumen of the access device; the wash fluid is introduced to a single breast milk duct and collected from the same breast milk duct without mixing with materials from other breast milk ducts. The volume of wash fluid can be at least 2 ml. The preselected time can be less than one second or in a range from one second to one hour. The method can further comprise separating cellular material from the collected fluid, and the separated material can be examined. The cellular material can be a substance selected from the group consisting of whole cells, cellular debris, nucleic acids, lipids, protein metabolites, small organic molecules, and macromolecules.

An aspect of the invention is a kit comprising a ductal access device; and instructions for use setting forth a method provided above comprising introducing a ductal access device having at least one lumen into a duct.

An aspect of the invention is a ductal access device comprising an access tube having a distal end, at least one lumen, and dimensions which permit introduction of the distal end through a ductal orifice and positioning a distal end distal to the ductal sphincter of a human breast. The device can further comprise means on the access tube for positioning the distal end distal to the ductal sphincter. The positioning means can comprise length indicia on the tube which permit a user to determine the depth to which the distal end of the tube has been introduced. The positioning means can comprise a stop element formed or attached to the tube; the stop will have dimensions which prevent further insertion of the tube into the duct and the stop is positioned on the tube so that the distal tip will be located distal to the ductal sphincter when the device is fully inserted up to the stop. The stop element can comprise a collar affixed to or formed on an exterior surface of the tube. The device can comprise means for anchoring the device to the breast. The device can include a receiving portion comprising a water tight seal for receiving the dilator. The stop element can comprise a hub attached to a proximal end of the tube, where the hub has a width which is greater than the diameter of the tube so that a shoulder is formed at a junction between the tube and the hub. The positioning means can comprise a nob on the access tube having an increase diameter for anchoring the tube in the lactiferous sinus once the nob has passed the sphincter and rests in the sinus. The access tube can have an outer diameter of 0.05 inches (or 1.27 mm) or less. The access tube can have an outer diameter of 0.010 inches (or 0.254 mm) or greater. The outer diameter can be in the range from 0.010 inches (or 0.254 mm) to 0.050 inches (or 1.27 mm). The access tube can have a lumen diameter 0.007 inches (or 0.178 mm) or greater. The access tube can have a lumen diameter in the range from 0.007 inches (or 0.178 mm) to 0.047 inches (or 1.19 mm). The access device can further comprise an infusion connector providing a fluid flow path into the lumen of the tube; and a collection connector providing a fluid outlet path from the lumen of the tube; the infusion and collection connectors are isolated from each other so that the fluid may be infused through the infusion connector and simultaneously removed through the collection connector. The device can further comprise a dilator removably received in the access tube and having a distal tip which is positionable through the access tube to extend from the distal end of the device. The dilator can have an outer diameter of 0.024 inches (or 0.61 mm) or less. The dilator can be tapered. A receiving portion of the device for receiving the dilator can comprise a water-tight seal.

An aspect of the invention is a ductal access system comprising a ductal access device as described and a container holding a premeasured volume of ductal wash fluid. The container can comprises a syringe for connection to the first side port. The pre-measured volume can be in the range from 2 ml to 100 ml. The ductal access fluid is can be selected from the group consisting of saline, phosphate buffered saline, a nonabsorbable fluid, an isotonic solution, an osmotic solution, a hypotonic solution, and a hypertonic solution.

A further aspect of the invention is a ductal access device comprising an access tube having a distal end, a single lumen, and dimensions which permit introduction of the distal end through a ductal orifice and positioning a distal end of the device distal to the ductal sphincter, an infusion connector providing a fluid flow path into the lumen of the access tube, and a collection connector providing a fluid outlet path from the lumen of the access tube; the infusion and collection connectors being isolated from each other so that fluid may be infused through the infusion connector and simultaneously removed through the collection connector. The tube has an outer diameter of 0.010 inches (or 0.254 mm) or greater or the tube has an outer diameter of 0.050 inches (or 1.27 mm) or less, or the outer diameter can be in the range from 0.010 inches (or 0.254 mm) to 0.50 inches (or 1.27 mm).

The access tube has a lumen diameter 0.007 inches (or 0.178 mm) or greater, or a lumen diameter in the range from 0.007 inches (or 0.178 mm) to 0.047 inches (or 1.19 mm). The device can further comprise means on the access tube positioning a distal end of the device distal to the ductal sphincter. The positioning means can comprise length indicia on the tube which permit a user to determine the depth to which the distal end of the tube has been introduced. The positioning means comprises a stop element formed or attached to the tube, and the stop has dimensions which prevent further insertion of the tube into the duct; the stop is positioned on the tube so that a distal end of the distal tip is positioned distal to the ductal sphincter. The stop element comprises a collar affixed to or formed on an exterior surface of the tube. The stop element can comprise a hub attached to a proximal end of the tube, where the hub has a width which is greater than the diameter of the tube so that a shoulder is formed at a junction between the tube and the hub. The positioning means can comprise a nob on the access tube having an increased diameter for anchoring the distal portion of the tube distal to the sphincter once the nob has passed the sphincter. The device can comprise means for anchoring the device to the breast. The device can additionally comprise a dilator removably received in the access tube and having a distal tip which is positionable through the access tube to extend from the distal end of access device. The dilator can have an outer diameter of 0.024 inches (or 0.61 mm) or less. The dilator can be tapered. A receiving portion of the device for receiving the dilator an comprise a water-tight seal.

An aspect of the invention is a ductal access system comprising a ductal access device as just described and a container holding a premeasured volume of ductal wash fluid. The container can comprise a syringe for connection to the first side port. The premeasured volume can be in the range from 2 ml to 100 ml. The ductal access fluid can be selected from the group consisting of saline, phosphate buffered saline, a nonabsorbable fluid, an isotonic solution, an osmotic solution, a hypotonic solution, and a hypertonic solution.

An aspect of the invention is a ductal access device comprising a hub having an internal elongate manifold, a lower port at a bottom of the manifold, and first and second side ports spaced above the lower port; and an access tube having a distal end, a proximal end, a lumen, and dimensions which permit introduction of the distal end through a ductal orifice and a positioning a distal end of the device distal to the ductal sphincter of the human breast, provided also that the proximal end of the tube is attached to the lower port of the hub. The first and second side ports can be at the same level relative to the lower port. The first side port can be below the second side port. The access tube can have an outer diameter of 0.010 inches (or 0.254 mm) or greater. The access tube can have an outer diameter of 0.50 inches (or 1.27 mm) or less. The outer diameter can be in the range from 0.010 inches (or 0.245 mm) to 0.50 inches (or 1.27 mm). The access tube can have a lumen diameter 0.007 inches (0.178 mm) or greater, or a lumen diameter in a range from 0.007 inches (0.178 mm) to 0.047 inches (1.19 mm). The device can have an infusion tube connected to the first port of the hub; and a collection tube connected to the second port of the hub. The device can further comprise a means for controlling a flow of fluid through the infusion tube, a means for controlling a flow of fluid through the collection tube, or both a means for controlling a fluid flow through the infusion lumen and a means for controlling a fluid flow through the collection lumen. The fluid control means can comprise compressable lumens or the fluid control means can comprise stopcocks on each lumen. The hub or manifold can have a volume in the range from 0.01 ml to 1.0 ml. The first side port can be spaced above the lower port by a distance less than 5 mm and the second side port can be spaced above the first side port by a distance in the range from 0.10 mm to 5 mm. The device can further comprise a dilator removably received in the hub and having a distal tip which is positionable through the access tube to extend from the distal end of the device. The dilator can have an outer diameter of 0.024 inches (or 0.61 mm) or less. The dilator can be positionable through the hub manifold and into the lumen of the access tube. The dilator can be tapered. A receiving portion of the hub for receiving the dilator can comprise a water-tight seal. The device can further comprise a means on the access tube for positioning the distal end of the access tube distal to the ductal sphincter. The positioning means can comprise length indicia on the tube which permit a user to determine the depth to which the distal end of the tube has been introduced. The positioning means can comprise a stop element formed or attached to the tube; the stop has dimensions which prevent further insertion of the tube into the duct and the stop is positioned on the tube so that the distal tip will be located distal to the ductal sphincter when the device is fully inserted up to the stop. The stop element can comprises a collar affixed to or formed on an exterior surface of the tube. The stop element can comprise a hub attached to a proximal end of the tube, where the hub has a width which is greater than the diameter of the tube so that a shoulder is formed at a junction between the tube and the hub. The device can further comprise a means for anchoring the device to the breast. The positioning means can comprise a nob on the access tube having an increased diameter for anchoring the tube distal to the ductal sphincter once the nob has passed the sphincter and rests distal to it.

An aspect of the invention is a ductal access system comprising a ductal access device as just described and a container holding a premeasured volume of ductal wash fluid. The container can comprise a syringe for connection to the first side port. The pre-measured volume can be in the range from 2 ml to 100 ml. The ductal access fluid can be selected from the group consisting of saline, phosphate buffered saline, a nonabsorbable fluid, an isotonic solution, an osmotic solution, a hypotonic solution, and a hypertonic solution.

An aspect of the invention provides a ductal access catheter comprising a catheter body having a distal end and a proximal end and including at least a distal portion and a proximal portion wherein the distal portion has a cross-sectional geometry which can be inserted through a ductal orifice into a ductal lumen of a human breast; wherein the proximal portion has a cross-sectional geometry which inhibits insertion through the ductal orifice and into the ductal lumen; and wherein the catheter body has at least an infusion lumen and an collection lumen each of which has a distal port near a distal end of the distal portion and a proximal connector near a proximal end of the proximal portion. The device can further comprise a means for controlling a flow of fluid through the infusion lumen, a means for controlling a flow of fluid through the collection lumen, or both a means for controlling a fluid flow through the infusion lumen and a means for controlling a fluid flow through the collection lumen. The fluid control means can comprise compressable lumens, or the fluid control means can comprise stopcocks on each lumen.

The distal portion of the catheter body can be stiffened over at least a part of its length to facilitate insertion through the ductal orifice and into the ductal lumen. The stiffened distal portion of the catheter body has an average bending stiffness in the range from about 0.010 inch-lbs to about 0.5 inch-lbs. The stiffening member is disposed in the distal portion of the catheter body.

The distal portion of the catheter body has a maximum width in the range from 0.016 inches to 0.022 inches (0.56 mm) and the proximal portion of the catheter body has a minimum width in the range from 0.023 inches (0.58 mm) to 0.028 inches (0.71 mm). The distal portion of the catheter body has a generally tubular structure with a diameter in the range from 0.010 inches (0.254 mm) to 0.020 inches (0.51 mm) and the proximal portion of the catheter body has a generally tubular structure with a diameter in the range from 0.030 inches (0.762 mm) to 0.10 inches (0.254 mm) and wherein the proximal diameter is greater than the distal diameter by at least 0.010 inches (or 0.254 mm). At least one of the distal collection port and the distal infusion portion can be disposed on a side of the distal portion of the catheter body. The distal collection port and the distal infusion port can both be located on the side of the distal portion of the catheter body. The distal collection port and the distal infusion port can be axially aligned. The distal collection port and the distal infusion port can be axially spaced apart. The catheter body can include an atraumatic distal tip. The tip can be composed of a soft polymeric material, have a diameter in the range from about 0.008 inches (0.20 mm) to about 0.035 inches (0.89 mm), and a length in the range from about 0.25 cm to about to 2.5 cm.

The invention further provides a ductal access catheter comprising a catheter body having a distal end and a proximal end and including at least a distal portion and a proximal portion; wherein the distal portion has a cross-sectional geometry which can be inserted through a ductal orifice into a ductal lumen of a human breast; wherein the distal portion of the catheter body is stiffened over at least a part of its length to facilitate insertion through the ductal orifice and into the ductal lumen; and wherein the catheter body has at least an infusion lumen and an collection lumen each of which has a distal port near a distal end of the distal portion and a proximal connector near a proximal end of the proximal connector. The stiffened distal portion of the catheter body can have an average bending stiffness in the range from about 0.010 inch-lbs to about 0.5 inch-lbs. The proximal portion can have a cross-sectional geometry that inhibits insertion through the ductal orifice and into the ductal lumen.

The invention also provides a ductal access catheter comprising a catheter body having a distal end and a proximal end and including at least a distal portion and a proximal portion; wherein the distal portion has a cross-sectional geometry which can be inserted through a ductal orifice into a ductal lumen of a human breast; and wherein the catheter body has at least an infusion lumen and an collection lumen each of which has a distal port near a distal end of the distal portion and a proximal connector near a proximal end of the proximal connector; and wherein the distal collection port and the distal infusion port are both located on the side of the distal portion of the catheter body. The distal collection port and the distal infusion port can be axially aligned. The distal collection port and the distal infusion port can be axially spaced apart. The proximal portion can have a cross-sectional geometry that inhibits insertion through the ductal orifice and into the ductal lumen.

Another aspect of the invention is a method for lavage of a ductal network in a human breast comprising providing a multi-lumen catheter as just described and inserting the distal portion of the catheter through a ductal orifice and into a distal lumen of the ductal network; introducing a wash fluid through the infusion lumen into the ductal network; and withdrawing the wash fluid and substances borne by the wash fluid from the ductal network through the collection lumen.

Another aspect of the invention is a system comprising a multi-lumen catheter as just described and instructions for use setting forth a method for lavage of a ductal network in a human breast including introducing a wash fluid through the infusion lumen into the ductal network and withdrawing the wash fluid and substances borne by the wash fluid from the ductal network through the collection lumen.

The agent infused into the duct can comprise a non-absorbable fluid and/or an oncotic agent and/or an osmotic agent. The agent can be soluble. The agent can comprise a molecule that is a protein, a colloid, a sugar, or a polymer. The agent can be mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, or a synthetic colloid. The agent can comprise a protein and the protein can be a binding protein or an antibody. The binding protein can be albumin. Administering can comprise administering locally, and local administration can comprise administering intra-ductally. A system for increasing or standardizing an amount of fluid collectable from a milk duct of a breast can comprise infusing a nonabsorbable fluid and/or an osmotic agent and/or an oncotic agent into the ductal lumen, a medical tool for delivering the agent to the ductal lumen, and instructions for use.

BRIEF DESCRIPTION OF THE DRAWINGS

FIG. 8 illustrates an alternative embodiment of the breast duct access device of the present invention.

FIGS. 8A and 8B are cross sectional views taken along lines 8A—8A and 8B—8B of FIG. 8, respectively.

FIG. 8C is a detailed view of the distal end of the device of FIG. 8.

FIG. 9A is a stepped transition zone.

DETAILED DESCRIPTION OF PREFERRED EMBODIMENTS OF THE INVENTION

Figure 1:
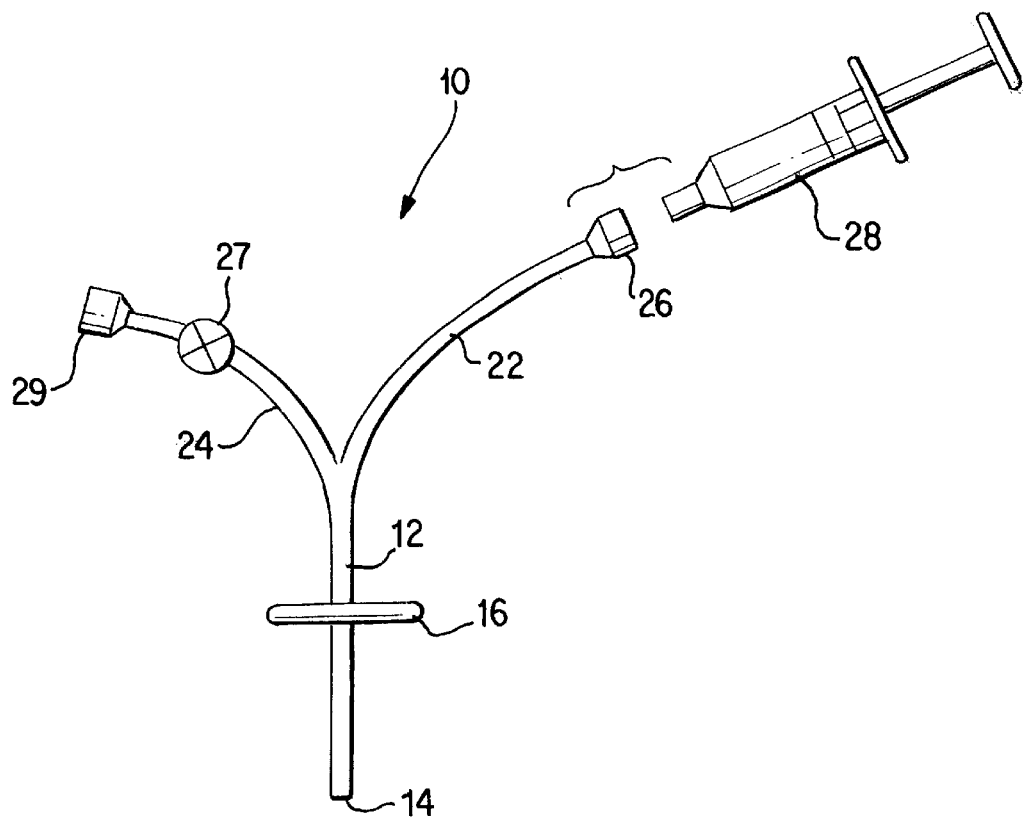
FIG. 1 shows a single lumen catheter with a stop and external infusion and collection tubes.

The following preferred embodiments and examples are offered by way of illustration and not by way of limitation.

The invention provides methods for obtaining cellular material from a human breast duct. A wash fluid is introduced and a volume of at least 2 ml is allowed to remain in the duct for a preselected time that can range from less than or about one second to about an hour, including any length of time in between. During the time that the wash fluid remains in the breast duct, it may mix with the ductal fluid already present in the duct, and it may accumulate cellular material either from the ductal lumen walls or that already present in the existing resident ductal fluid. The breast duct may be filled with wash fluid before the wash fluid mixed with ductal fluid and comprising cellular material is collected. For example, a wash fluid may be infused into the duct until a point of resistance to infusion, a which point it may be considered that the breast duct may is filled with wash fluid, and the just infused fluid can be allowed to reside in the duct for a preselected time. Once the time has elapsed, the infused fluid and the contents of the duct with which it has mixed is collected. If a ductal access tool is used to access the duct and infuse the fluid into the duct, the in-dwelling tool can obtain or collect the infused fluid either through the same lumen that was used to infuse the wash fluid into the duct originally, or through a separate second lumen adjacent or coaxial to the infusion lumen. In any event the access tool remains in place in the duct during the infusion, filing, preselected waiting time (e.g. less than one second or about one second to one hour), and collection of the wash fluid mixed with ductal fluid and cellular material from the breast duct.

Methods of the invention include accessing a single breast duct and obtaining cellular material from that duct without allowing the cellular material or ductal fluid from the accessed duct to contact the cellular material or ductal fluid of any other duct, or cellular material or ductal fluid that happens to be residing on the nipple surface. Thus is provided the opportunity to analyze a single individual breast duct separate from other breast ducts of the patient. The wash fluid can be introduced into the duct by accessing the breast duct with a ductal access device having at least one lumen. Infusion of wash fluid into the duct is provided through the lumen accessing the duct. Collection of the wash fluid mixed with ductal fluid and comprising cellular material can also be provided through the lumen accessing the duct. Access of a single breast duct provides also the opportunity to collect ductal fluid and cellular material from the accessed breast duct separate from other breast ducts on the breast, without mixing or contacting the collected fluids and cellular material with that of the other ducts, and so providing the opportunity to analyze the condition of the accessed duct separately.

During the procedure the breast may be massaged and squeezed. Massaging and squeezing the breast may facilitate collection of the infused fluid and mixed ductal fluid and cellular material. The actions of massaging and squeezing the breast may also provide some disruption of the cells on the lumen walls, thereby increasing a yield of cellular material from the procedure. Collection from a collection lumen (either the same lumen as was used to infuse or a separate lumen) can be further facilitated in some cases with aspiration applied into the lumen. Preferably, where an indwelling tool is used, a single lumen accesses the breast duct, and external to the breast and breast duct the tool branches into an infusion lumen and a collection lumen. From this collection lumen, during the period when the fluid is being collected from the duct, aspiration may be applied.

Additionally, where a manifold hub is present in the design of the access tool, once the wash fluid mixed with ductal fluid and cellular material is passed out of the duct and into the hub, collection may be facilitated from the collection lumen without risk of collapsing the ductal wall, but providing an aspiration pressure in the collection lumen (e.g. using a syringe and pulling back to collect material into the syringe). Additionally, or alternatively, the hub filled with collected material may be flushed into the collection lumen using an infusion of wash fluid from the infusion lumen. The fluid flow into and out of the infusion and collection lumens may be facilitated with means on the device lumens to stop or open the fluid flow into or out of the lumens.

Additionally, when a ductal access device is used to access a breast duct, the distal end of the device comprising an infusion and/or collection port or ports is placed distal to the ductal sphincter to provide an optimal position for infusion and collection of fluid and/or other agents or materials to and from the breast duct. Means to assure placement of the distal tip of the device distal to the ductal sphincter can be provided on the device as further discussed below in the ductal access device design.

The wash fluid that is introduced into the duct can comprise any biocompatable agent or solution. Thus, the wash fluid can comprise e.g. saline, phosphate buffered saline. Additionally or alternatively, the wash fluid can comprise an agent or agents or solution that reduces the ability of the fluid or agent to diffuse through the ductal wall or otherwise leave the duct and enter other parts of the body. Accordingly, the wash fluid may comprise a nonabsorbable fluid, an isotonic solution, an osmotic solution, a hypotonic solution or a hypertonic solution. Fluid or agents may be administered to the breast duct in order to facilitate, increase, and/or optimize the amount of material obtained or obtainable from the breast duct during the procedure. Agents or solutions that may comprise the infused wash fluid can include, e.g. protein, colloid, sugar, polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, albumin, a synthetic colloid, an antibody or part of an antibody, or a binding protein.

Once the wash fluid had been infused in the duct and the wash fluid and ductal fluid is collected from a breast duct, the cellular material can be separated and can be examined. The cellular material can include, e.g. substances selected from the group consisting of whole cells, cellular debris, proteins, nucleic acids, polypeptides, glycoproteins, lipids, fats, glycoproteins, small organic molecules, metabolites, and macromolecules. Whole cells can be examined by cytology, or any other suitable method for analyzing the condition of the cells. Other markers present in the cellular material, ductal fluid generally, or other material obtained from the breast duct can be analyzed as is appropriate for the marker being sought, including e.g. binding assays, immunohistochemistry, or using other analytical technology for distinguishing and identifying biological molecules obtained from biological material.

Chromosomal abnormalities in ductal epithelial cells can also provide information and act as a marker to identify cancer or precancer as described in Mark et al (1999) *Cancer Genet Cytogenet* 108:26–31; Lundlin and Mertens (1998) *Breast Cancer Res Treat* 51:1–15; Newsham (1998) *Am J Pathol* 153:5–9; Larson et al (1998) *Am J Pathol* 152:1591–8; Adelaide et al (1998) *Genes Chromosomes Cancer* 22:186–99; Fejzo et al (1998) *Gene Chromosome Cancer* 22:105–113; Dietrich et al (1998) *Hum Pathol* 12: 1379–82; Cavalli et al (1997) *Hereditas* 126:261–8; Adeyinka et al (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al (1997) *Ann Clin Lab Sci* 27:47–56; and Fabian et al 1993 *J. Cellular Biochemistry* 17G:153–16.

In addition, exemplary markers are described in Masood S., (Prediction of recurrence for advanced breast cancer. Traditional and contemporary pathologic and molecular markers) *Surgical Oncology Clinics of North America.* 4(4): 601–32, 1995; Lopez-Guerrero et al (1999) *J Hematother* 8(1):53–61; Marjumdar and Diamandis (1999) *Br J Cancer* 79(9–10):1594–602; Balleine et al (1999) *Br J Cancer* 79 (9–10):1564–71; Houston et al (1999) *Br J Cancer* 79(7–8): 1220–6; Nikolic-Vukosavljevic et al (1998) *Tumori* 84(6): 691–4; Maguire et al (1998) *Int J Biol Markers* 13(3): 139–44; Stearns et al (1998) *Breast Cancer Res Treat* 52(1–3):239–59; Eiriksdottir et al (1998) *Eur J Cancer* 34(13):2076–81, and U.S. Pat. No. 5,169,774. Many known breast cancer markers are discussed and described in readily available medical text books on breast cancer. In addition, several markers can be identified and analyzed in the same sample, e.g. Fabian et al 1993 *J. Cellular Biochemistry* 17G: 153–16 and Fabian et al 1994 *Breast Cancer Res Treat* 30(3):263–74 looking at estrogen receptor (ER), epidermal growth factor receptor (EGFR), mutant p53, HER-2 neu by immunohistochemistry and aneuploidy by image analysis in fine needle aspirates.

Cytological assays that can be performed on the cells retrieved from a duct or from nipple aspirate can include e.g. assays described in King et al, *J. Nat'l Cancer Inst* (1983) 71:1115–21, Wrensch et al. (1992) *Am. J. Epidem.* 135: 130–141, Papanicolaou et al, (1958) *Cancer,* 11:377–409 and Goodson W H & King E B, Chapter 4: *Discharges and Secretions of the Nipple,* The Breast: Comprehensive Management of Benign and Malignant Diseases (1998) 2$^{nd}$ Ed. vol 2, Bland & Kirby eds. W. B. Saunders Co, Philadelphia, Pa. pp. 51–74. For example, as described in Goodson and King (page 60) atypical hyperplasia presents as having cellular abnormalities, increased coarseness of the chromatin, and tendency for more single cells as well as groups of cells. With regard to carcinoma in situ, Papanicolaou et al, described cellular abnormalities, e.g. nuclear abnormalities diagnosed by cytology of fluid from nipple secretions containing ductal cells. The cytology of abnormal cells can also be conducted as described in Sartorius et al (1977) *J. Natl Cancer Inst* 59: 1073–1080. and King et al, (1983) *JNCI* 71(6) 1115–1121. Atypia and carcinoma in situ are widely characterized pathologically, as described in Page et al, (1998) *Mod Pathol* 11(2): 120–8. The ductal fluid can be analyzed by cytological techniques by placing some of the fluid on a slide with a standard cytological stain using a light microscope. The cells can be studied for atypical growth patterns in individual cells and clusters of cells using published methods, including Mouriquand J, (1993) S Karger Pub, "Diagnosis of Non-Palpable Breast Lesions: Ultrasonographically Controlled Fine-Needle Aspiration: Diagnostic and Prognostic Implications of Cytology" (ISBN 3805557477); Kline T S and I K, Pub Igaku-Shoin Medical "Breast: Guides to Clinical Aspiration Biopsy" (LSBN 0896401596; Masood, *American Society of Clinical Pathology: November* 199S, "Cytopathology of the Breast" ISBN 0891893806; and Feldman P S, *American Society of Clinical Pathology, November* 1984, "Fine Needle Aspiration Cytology and Its Clinical Applications: Breast and Lung" ISBN 0891891846.

Other references that discuss cytological analysis and which give guidance to an analysis of ductal epithelial cells derived from ductal fluid include Silverman et al, (Can FNA biopsy separate atypical hyperplasia, carcinoma in situ, and invasive carcinoma of the breast?: Cytomorphologic criteria and limitations in diagnosis, Diagnostic Cytopathology) 9(6):713–28, 1993; Masood et al, (Immunohistochemical differentiation of atypical hyperplasia vs. carcinoma in situ of the breast) *Cancer Detection & Prevention.* 16(4): 225–35, 1992; Masood et al, (Cytologic differentiation between proliferative and nonproliferative breast disease in mammographically guided fine-needle aspirates) *Diagnostic Cytopathology.* 7(6):581–90, 1991; Masood S., (Occult breast lesions and aspiration biopsy: a new challenge) Diagnostic Cytopathology. 9(6):613–4, 1993; Masood S., (Prognostic factors in breast cancer: use of cytologic preparations) *Diagnostic Cytopathology.* 13(5):388–95, 1995; Novak and Masood, (Nuclear grooves in fine-needle aspiration biopsies of breast lesions: do they have any significance?) *Diagnostic Cytopathology.* 18(5):333–7, 1998; Sidawy et al, (Interobserver variability in the classification of proliferative breast lesions by fine-needle aspiration: results of the Papanicolaou Society of Cytopathology Study) *Diagnostic Cytopathology.* 18(2):150–65, 1998; Masood et al, (Automation in cytology: a survey conducted by the New Technology Task Force, Papanicolaou Society of Cytopathology) *Diagnostic Cytopathology.* 18(1):47–55, 1998; and Frykberg and Masood Copeland E M 3d. Bland K I., (Ductal carcinoma in situ of the breast) *Surgery, Gynecology & Obstetrics* 177(4):425–40, 1993.

Appropriate animal models for breast cancer therapies have been described, e.g. McKenzie and Sukumar, (Molecular mechanisms of chemical carcinogenesis in rodent models) *Cancer Treatment & Research* 71:313–29, 1994; Chen et al, (Midkine in the progression of rat N-nitroso-N-methylurea-induced mammary tumors) *Molecular Carcinogenesis.* 17(3):112–6, 1996; and Sukamar et al, (Animal models for breast cancer) *Mutation Research* 333(1–2):37–44, 1995.

In addition to some markers discussed and/or articles or books cited on breast cancer and breast precancer markers, the following cancer markers are listed here as exemplary and may be used as well as other markers to analyze the condition of a breast duct. Standard assay procedures for identifying the markers can be used, including antibodies or other binding partners, labels, stains, pattern analysis (for cells and cell components), and in general any other chemical or visual identification techniques. The following are exemplary potential markers for such identification and analysis: cathepsins (including cathepsin D); maspin, fas, fas ligand, tissue inhibitor of matrix metalloproteinas-1 (TIMP-1); chemokines (both C-C and C-X-C type chemokines); collagenases, metalloproteinases, TIMP's, cathepsins, disrupted basement membrane epitopes, stromolysin-3; cytokeratins (e.g. keratin 14, B1, KA1, KA4 and 312C8-1);

estrogen and progesterone receptors (or any androgen or other steroid receptor); growth factor receptors for members of the fibroblast growth family (FGF) including FGF1–18, vascular endothelial growth factor (VEGF), insulin-like growth factor –1 (IGF-I), IGF-II, platelet-derived growth factor (PDGF), keratinocyte growth factor (KGF), and epithelial growth factor (EGF); placental growth factor (PLGF), hepatocyte growth factor (HGF), tumor necrosis factor (TNF), transforming growth factor (TGF) both alpha and beta forms, and angiopoietin, for example; growth factors and cytokines including e.g. FGF1–18, VEGF, IGF-I, IGF-II, PDGF, KGF, EGF, PLGF, HGF, TNF, TGF alpha and beta, angiopoietin; heat shock proteins (HSP) (e.g. HSP27) 27 (HSP27); ErB type 1 tyrosine kinase receptors (e.g. Her2 (an EGF receptor) or any ligand or receptor of the ErbB family of ligands and receptors); integrins, selectins, cadherins, for example (i.e. alpha and beta 3 integrin); keratin-14; known cancer antigens including, for example Ki-67, Ki-S1, p53, nm23, bcl-2, p21 ras, cyclins, and pS2; thrombin receptor activating peptide; urokinase, urokinase-type plasminogen activator (UPA), plasmin antiplasmin; UPA receptor (UPAR), fibrinogen, plasmin activator inhibitor-1 and 2 (PAI-1 and 2); telomerase; antibodies to tumor associated antigen-72 (TAG-72) (e.g. B72.3, B6.2, and TKH2); carcinoembryonic antigen (CEA) (see e.g. EP 319,686); prostate specific antigen (PSA); gross cystic disease fluid protein-15 (GCDFP-15); lactose dehydrogenase (LDH); chromosomal abnormalities (e.g. aneuploidy or other abnormalities); S1 protein; alkaline phosphatase; myosin; sialyl Tn (STn) glycopeptide (e.g. TAG-72); Tn glycopeptide; and nuclear matrix proteins provisional application No. 60/166,100 (as described in provisional patent application filed Nov. 17, 1999 herein incorporated by reference in its entirety).

In general, markers can be categorized nonexclusively, and often in overlapping categories as follows: 1. Markers that are detected or detectable by virtue of protein expression or overexpression (detection may occur, e.g. by immunohistochemistry or in situ hybridization); 2. Markers that are detected or detectable by virtue of mRNA expression or overexpression (detection may occur, e.g. by differential display techniques); 3. Markers that are detected or detectable by virtue of a post translational change in a protein, e.g. a phosphorylation of the protein, a ubiquitination, a farnesylation, methylation, or other modification to the protein that can be detected, e.g. by antibodies specific to the post translational modification.

Accordingly, markers such as the following can sought in ductal fluid, e.g. proteins that are overexpressed, mRNA transcripts that are over expressed, and proteins comprising post translational modifications. For example, the following markers can be identified to distinguish a cancer or precancer cell from a normal cell. Proteins that are overexpressed can include e.g. Stromelysin-3, Membrane Type 1 Matrix Metalloproteinase (MT1-MMP), Matrix Metalloproteinase-3 (MMP-3), Placental Isoferrintin (p43), Nuclear Matrix Protein (NMP22), NM-200.4 specific antigen, Vascular Endothelial Growth Factor (VEGF), Endoglin (CD105), Telomerase, ErbB-2, ErbB-3, Carcinoembryonic Antigen (CEA), Heat Shock protein-27 (HSP-27), Breast Cancer-specific Gene (BCSG), Plasminogen Activator Inhibitor (PAI-1), Urokinase Plasminogene Activator (uPA), Urokinase Plasminogene Activator Receptor (uPAR), Colony Stimulating Factor-1 (CSF-1), Colony Stimulating Factor-1 receptor (fms), Annexin I, Vasopressin, the CC Chemokine Regulated on Activation Normal T cell Expressed and Secreted (RANTES), 44-3A6 specific antigen, A-80 specific antigen, MUC-1, H23 specific antigen, 83 D4 specific antigen, SP-2 specific antigen, 323/A3 specific antigen, tumor associated antigen-72 (TAG-72), and MBE6 specific antigen.

Other breast cancer markers detected by any means including e.g. protein expression, mRNA expression, or post translational modification can include e.g. (listed alphabetically) alanine aminopeptidase, alpha 6 integrin, alpha-lactalbumin, AN43, p53, Bcl2-antagonist of cell death (Bad), Bcl2-associated athanogene (BAG-1), Bcl2-antagonist/killer 1 (Bak), Bcl2-associated X protein (Bax), Breast cancer antigen 225 (BCA225), B-cell CLL/lymphoma 2 (Bcl-2), Bcl2-like 1 (Bcl-x), beta 1–6 branched oligosaccharides, beta-2 microglobulin (BMG), Bcl2 related protein A1 (Bfl-l), bone sialoprotein (BSP), CCAAT/enhancer-binding protein liver-enriched inhibitory protein (C/EBPbeta-LIP), Carcinoma Antigen 1 (Ca 1), Carcinoma Antigen 27.29 (CA 27.29), Carcinoma Antigen M26 (CA M26), Carcinoma Antigen M29 (CA M29), Carcinoma Antigen 125 (CA125), Carcinoma Antigen 15.3 (CA15.3), Carcinoma Antigen 195 (CA195), Carcinoma Antigen 19-9 (CA19-9), Carcinoma Antigen 50 (CA50), Carcinoma Antigen 549 (CA549), Cadherin-11, calcitonin receptor (CTR), cathepsin B, cathepsin L, Endoglin (CD105), CD24, CD34 (pan-endothelial marker), CD44, c-met/hepatocyte growth factor receptor, c-myc, cyclooxygenase-1 (Cox-1), cyclooxygenase-2 (Cox-2), caspase-3 (CPP32), Cyclic nucleotide phosphodiesterase, cycline E, DNA topoisomerase II-alpha, DNA topoisomerase II-beta, EGF, EGF receptor, E-selectin, fast homoarginine-sensitive alkaline phosphatase (FHAP), fatty acid synthase, ferritin, gross cystic disease fluid protein (GCDFP-15/BRST-2), metastasis-associated h-mts1 (S100A4), heat shock cognate protein-73 (hsc73), heat shock protein-70 (hsp70), heat shock protein-90 alpha (hsp90alpha), heat shock protein-90 beta (hsp90beta), inhibitors of differentiation-1 (ID1), inhibitors of differentiation-3 (ID3), interleukin-1 beta, Keratin 8, Keratin 18, Keratin 19, Laminin, Laminin receptor (MLuC5), Leucine Aminopeptidase (LAP), lipid-bound sialic acid (LSA), Melanoma antigen-1 (MAGE-1), Melanoma antigen-2 (MAGE-2), Melanoma antigen-3 (MAGE-3), Man6-P glycoproteins, Mucin-like carcinoma associated antigen (MCA), myeloid cell leukemia-1 (Mcl-1), metallothionein (MT), mitogen-activated protein kinase phosphatase-1 (MKP-1), Matrix Metalloproteinase-2 (MMP-2), Matrix Metalloproteinase-9 (MMP-9), mammary serum antigen (MSA), breast cancer mucin-2 (MUC-2), breast cancer mucin-3 (MUC-3), breast cancer mucin-6 (MUC-6), Nm23 nucleoside diphosphate kinase, ornithine decarboxylase (ODC), osteopontin (OPN), P114 (MAR binding protein), P120 (a nucleolar proliferation antigen), focal adhesion kinase p125FAK, nuclear autoantigen p330d/CENP-F, plasminogen activator inhibitor-2 (PAI-2), Pepsinogen C, placental alkaline phosphatase (PLAP), Platelet factor 4 (angiogenic marker), protein kinase C (PKC), prostate specific antigen (PSA), pyrimidine nucleoside phosphorylase, ras p21, reduced glutathione (GSH), retinoid X receptor alpha, ribosomal S2 protein, sialyltransferase, Stromelysin-1 (MMP-3), surfactant proteins A, surfactant proteins B, tumor associated antigen-12 (TAG-12), trefoil gene TFF1, trefoil gene TFF3/ITF/hP1.B, Thrombin, Thrombomodulin, thymidine phosphorylase (TP), thymosin beta 15, tissue cytosol ferritins, tissue polypeptide antigen (TPA), tissue polypeptide specific antigen (TPS), Vascular Endothelial Growth Factor -B (VEGF-B), Vascular Endothelial Growth Factor-C (VEGF-C), Vascular Endothelial Growth Factor receptor-1 (VEGFR1), Vascular Endothelial Growth Factor receptor-2 (VEGFR2), and Vascular Endothelial Growth Factor receptor-3 (VEGFR3).

Some Genes are overexpressed and can be found by differential display, including e.g. Claudin-7, Zinc-alpha-2-glycoprotein, Apolipoprotein B, B94, EST (R08988), Thrombospondin (THBS1), FGF-1, NGAL/Lipocalin 2, EST (N77731), BS247 [Abbott Labs WO 9922027], AIB-1. Post translational modifications can be identified in proteins, including e.g. Tyrosine phosphorylation, ErbB-2, and EGFR. Absence of key tumor suppression markers include e.g. mammastatin and maspin.

Turning now to the figures, FIG. 1 provides a ductal access device 10 comprising an access tube 12 having a distal end 14, at least one lumen therethrough, and dimensions which permit introduction of the distal end through the ductal orifice and positioning a distal end thereof distal to the ductal sphincter of a human breast, e.g., typically having an outer access tube diameter in the range from 0.5 mm to 1 mm, preferably being tapered within this range over a length from 2 to 3 mm. The device can also comprise means on the access tool for positioning the distal end distal to the ductal sphincter. The device can have a stop 16 or other means to prevent the device from penetrating the duct too deeply. Alternatively, the tube could have a shoulder or other enlargement to block penetration at a point at which it is desirable to stop the penetration of the tool; or, alternatively, a collar can be placed or built onto the external portion of the access tube to prevent penetration beyond the collar.

Figure 2:
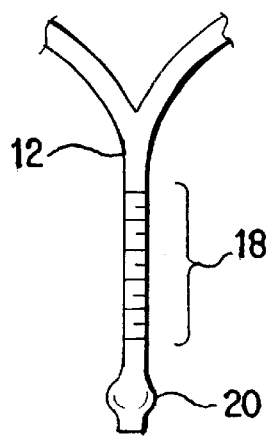
FIG. 2 is a detailed view of a calibrated ductal access portion of a single lumen catheter. The calibration serves to identify a depth of penetration.

The means provided to position the device distal to the ductal sphincter can comprise marks 18 on the access portion of the device to indicate a penetration depth as indicated in FIG. 2. Additionally, it may be desired that the device is anchored just distal to the ductal sphincter once the distal tip has passed through the ductal sphincter. This may be facilated by any number of means, including, e.g. placing a small nob or hub 20 on the tube 12 which acts as a stop to resist removing the distal tip once the nob has passed by the ductal sphincter and resides distal to it. Anchoring the distal tip of the ductal access device distal to the ductal sphincter may also be accomplished by placing the distal tip to a depth beyond the ductal sphincter and inflating a balloon (not shown) to anchor the device below the ductal sphincter during the infusion and collection procedure.

The device may also comprise a stop or hub or other means for keeping the tube accessing the duct from penetrating too far, and for positioning the access tube distal to the ductal sphincter. Thus, the device may include a positioning means comprising a stop element formed or attached to the tube. The stop element has dimensions which prevent further insertion of the tube into the duct, and the stop is positioned on the tube so that the distal tip will be located distal to the ductal sphincter when the device is fully inserted up to the stop, thus ensuring correct positioning of the tube in the duct relative to the ductal sphincter. The access lumen will terminate in at least one port for fluid infusion and/or collection, and the port is preferably placed at the end of the distal tip of the device so that it opens in a distal (axial) direction relative to the access tube 12, and the port is preferably located relative to the stop element so that the port resides distal to the ductal sphincter when the stop element engages the nipple. The stop element can comprise a hub attached to a proximal end of the tube, wherein the hub has a width which is greater than the diameter of the tube so that a shoulder is formed at a junction between the tube and the hub.

The access device can also be anchored to the external portions of the accessed breast by any means capable of accomplishing the anchoring. During the procedure it is important that the access device not slip out of the duct. Portions of the device that are external to the access breast duct can be affixed, strapped, tethered, taped, or otherwise anchored to the breast during the procedure in order to ensure that the device does not slip out of the duct. Such anchoring also provides the practitioner with better control of the device parts if part or all of the device is anchored, and therefore does not need to be held by the practitioner or an assistant.

In a preferred aspect of the catheter design, the access tube 12 will branch into an infusion arm 22 and collection arm 24. The infusion arm 22 terminates in a connector 26 which removably connects to a syringe 28 or other pressurized source of wash fluid. The collection arm 24 will preferably include a valve 27 and an end connector 29 for removable attachment to a collection apparatus, such as a vial, tube, tray, microliter plate, another syringe, or the like. As discussed below, the collection arm will usually be closed, e.g., with valve 27, during infusion of the wash fluid. Preferably, both the infusion arm lumen and collection arm lumen will be connected to a single lumen within the access tube 12.

Figure 3:
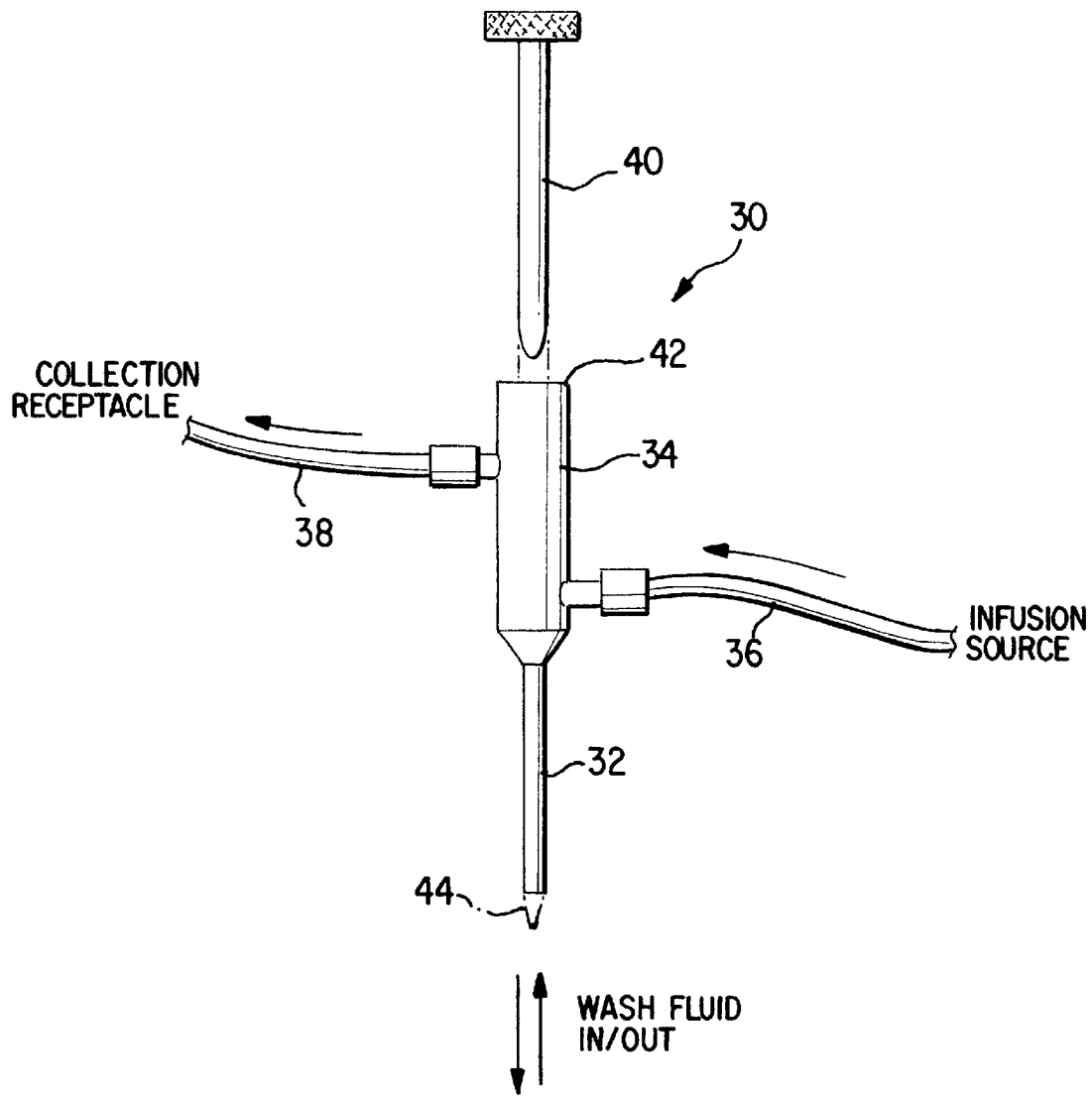
FIG. 3 is a single lumen ductal access catheter having a hub and infusion and collection lumens and a retractable dilator.

Turning now to FIG. 3, a preferred embodiment of the device is shown in a single lumen ductal access device 30 having a tube 32 that accesses the duct and through which fluid is infused, and from which fluid is collected or drawn up out of the duct. A hub 34 is connected to an infusion tube 36 from which fluid is infused into the access tube 32 and a collection tube 38 from which fluid is collected from the access tube. The collection tube 38 is preferably attached to the hub 34 at a position no closer to the access tube 32 than the infusion tube 36. Preferably, the collection tube 38 is located further away from the access tube 32 than is the infusion tube 36. A stylet 40 is optionally provided to facilitate introduction of the access tube through a ductal orifice into a ductal lumen. The stylet 40 will pass through a pneumostatic seal at a proximal end 42 of the hub 34 so that the stylet can be removed after positioning of the access tube 32 and prior to the infusion/collection of the wash fluid.

Fluid is infused into the hub 34 and into the duct until resistance is met during the infusion. At this time, it is assumed that the duct is filled. The infusion lumen can be closed and the fluid allowed to remain in the duct for a preselected time. During this preselected time, the breast may be massaged and squeezed to stimulate mixing of the wash fluid and ductal fluid, and also ultimately to encourage the fluid to leave the duct and enter the manifold hub. The collection lumen is opened and the breast squeezed to urge the fluid to progress through the access tube in the hub. If desired, when cloudy return fluid is seen in the hub (which is preferably transparent or includes a transparent window), the infusion lumen can be opened and fluid infused to push the fluid that has collected in the hub into the collection lumen and a waiting collection receptacle. Alternatively, and possibly additionally, aspiration pressure can be applied at the collection lumen to aspirate any fluid remaining in the hub into the collection receptacle. The process is repeated either following another infusion of fluid into the duct or by another round of squeezing to encourage return and collection of the infused fluid.

The stylet 40 can be made of metal or hard plastic and may have a tapered and/or an atraumatic tip for gently probing and accessing a breast duct. Preferably, a tapered tip 44 will extend distally of the access tube 32 as the tube is introduced. After access of the duct is complete, the stylet 40 can be withdrawn and the access tube positioned so that its distal end is distal to the ductal sphincter. The dilator receiving portion at the proximal end of the device can be a water tight membrane or sheath to provide a sterile environment in the hub even with penetration and withdrawal of the dilator, and to provide an appropriate amount of resistance so that the probe can be manipulated into and out of the duct and the access tube. The dilator shown in FIG. 3 is removably received in the access tube and has a distal tip which is positionable through the access tube to extend from the distal end of the access tube. In addition to providing tapered access, the stylet 40 selectively stiffens the access tube to further ease introduction into and through the ductal orifice. The access tube 32 may have an outer diameter in a range from about 0.25 mm to 1.25 mm with an inner lumen diameter in the range from 0.2 mm to 1.2 mm.

Figure 3A:
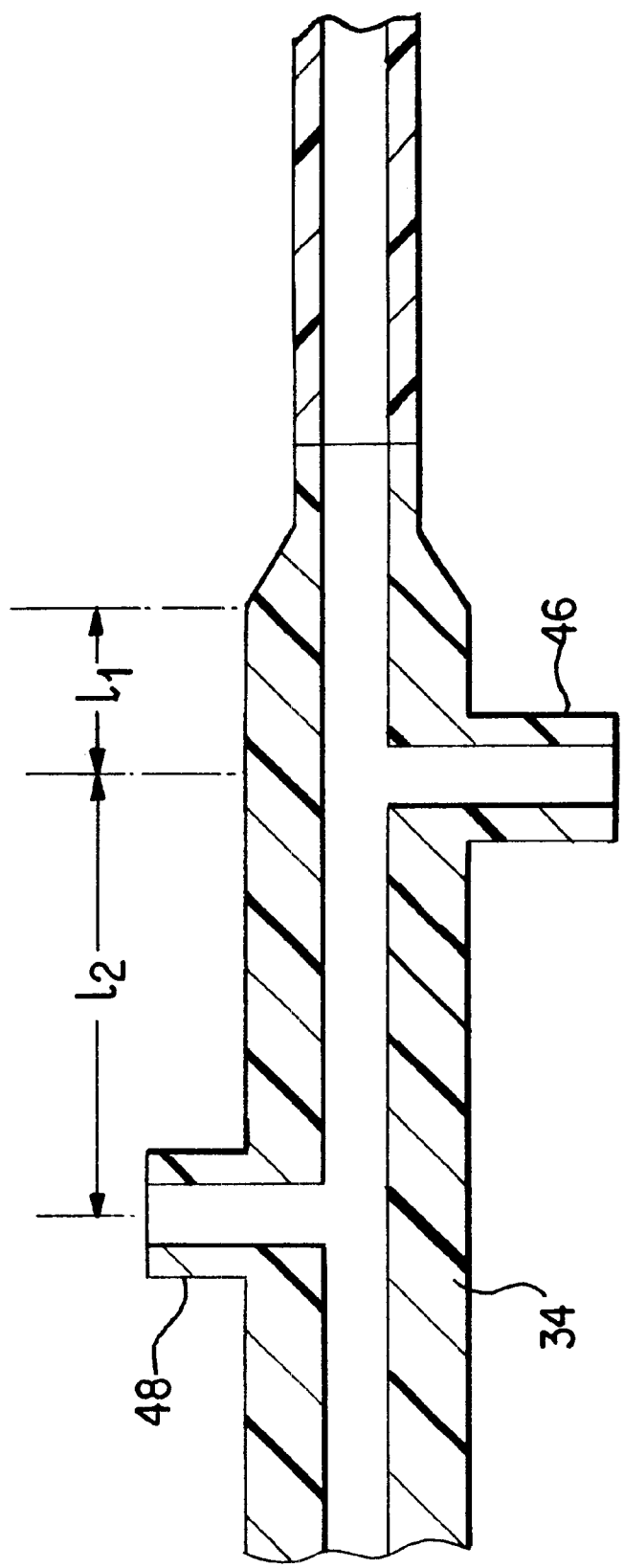
FIG. 3A is a cross section of the device in FIG. 3.

As illustrated in FIG. 3A, the hub 34 can have an infusion connector 46 providing a fluid outlet path into the lumen of the tube 32, and a collection connector 48 providing a fluid outlet path from the lumen of the tube. These infusion and collection connectors are preferably isolated from each other so that the fluid may be infused through the infusion connector and simultaneously removed through the collection connector. The distance $l_1$ between the infusion port 46 and access tube 32 is preferably minimized, usually being 1 cm or less, while the distance $l_2$ between the infusion port 46 and collection port 48 may be from 0 mm to 2 cm, preferably being 1 cm or less. While illustrated on opposite sides of the hub 34, the infusion port 46 and collection port 48 may have any relative radial orientation, with an alignment of both ports on the same side of the hub being presently preferred.

Figure 4A:
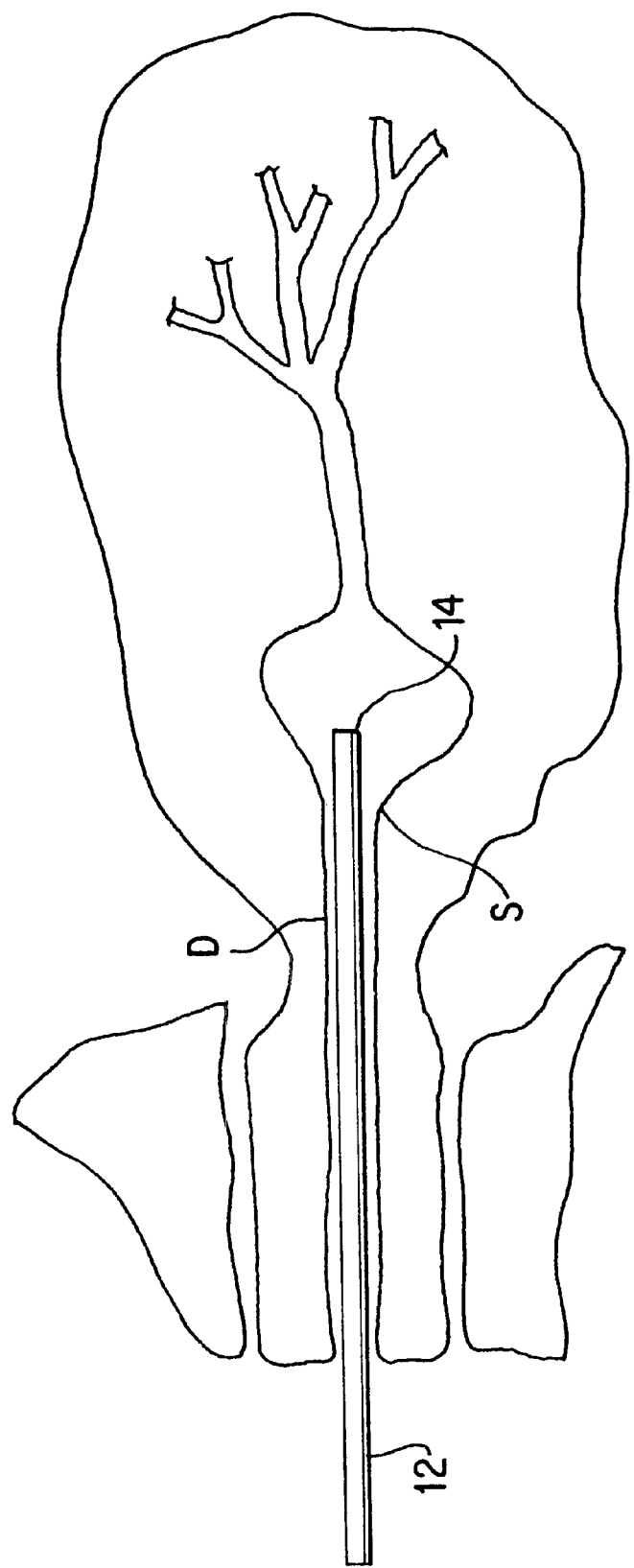
FIG. 4A illustrates access of a breast duct and penetration to at least a region distal to the ductal sphincter.
Figure 4B:
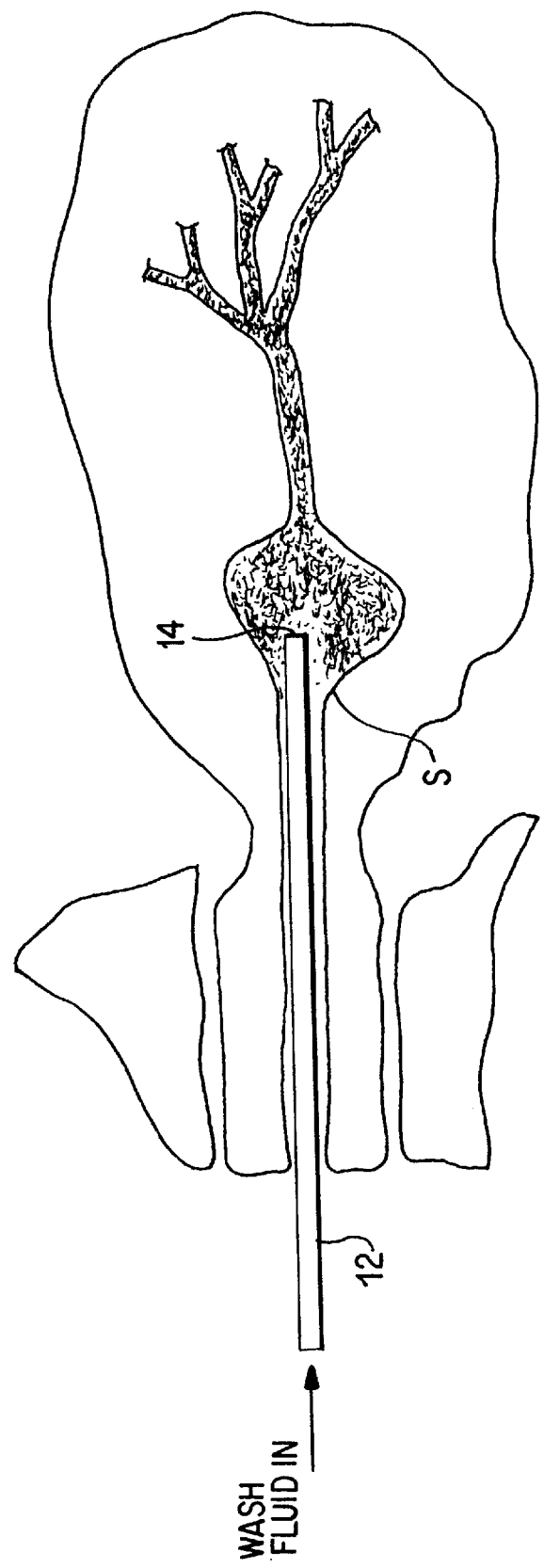
FIG. 4B illustrates filling a duct with infusion fluid.
Figure 4C:
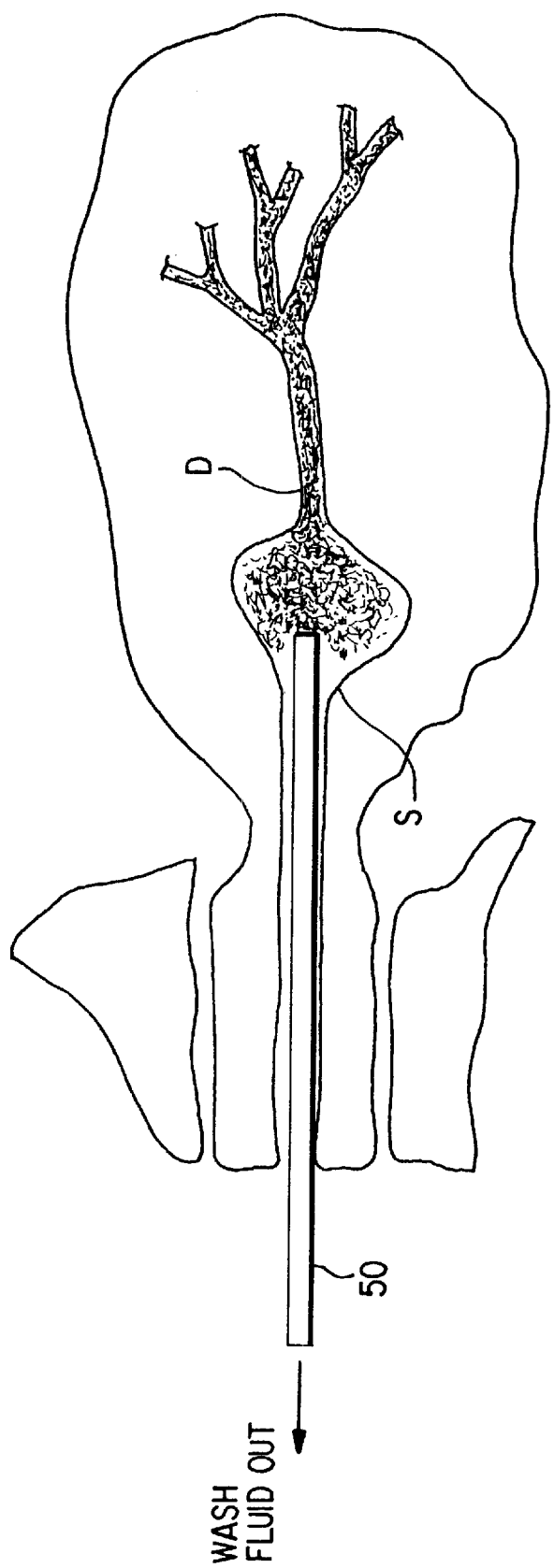
FIG. 4C illustrates bidirectional flow of infused fluid in the duct through the access lumen to be collected.
Figure 4D:
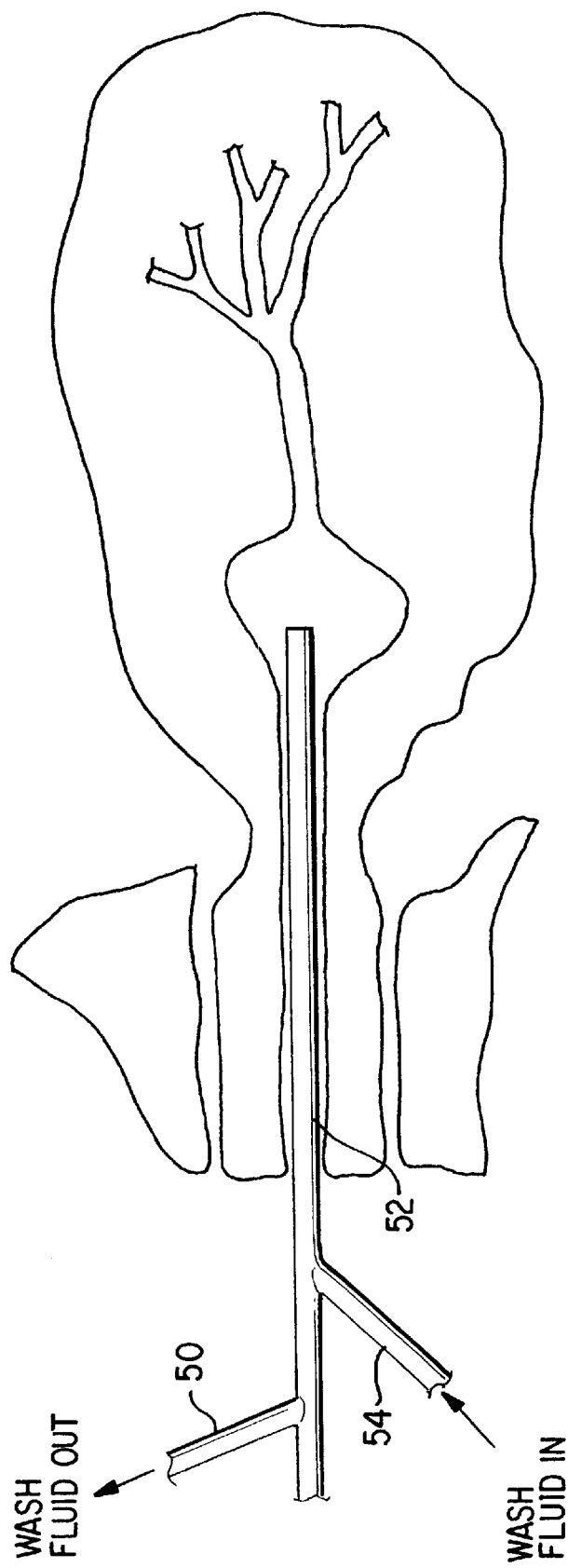
FIG. 4D illustrates a single lumen catheter accessing a breast duct having the capacity to infuse and collect fluid outside the accessed breast duct.

FIG. 4A depicts a single lumen access tube 50 accessing the breast duct D and positioned with its distal end 14 distal to the ductal sphincter S of the breast duct. FIG. 4B depicts filling the breast duct D and allowing the fluid to remain in the duct for a preselected time. FIG. 4C depicts removing the infused fluid mixed with ductal fluid through the access tube that remains in the duct during the filling of the duct and collecting of the fluid. FIG. 4D depicts a catheter 52 having infusion and collection arms 54 and 56 exterior to the accessed duct for separately infusing fluid into the duct and collecting fluid from the duct. The invention provides a device having an access tube, a distal end, a single lumen, dimensions to permit insertion of the device distal to the ductal sphincter. The device also has an infusion connector, a collection connector, and that the infusion and collection connectors are isolated.

Figure 6:
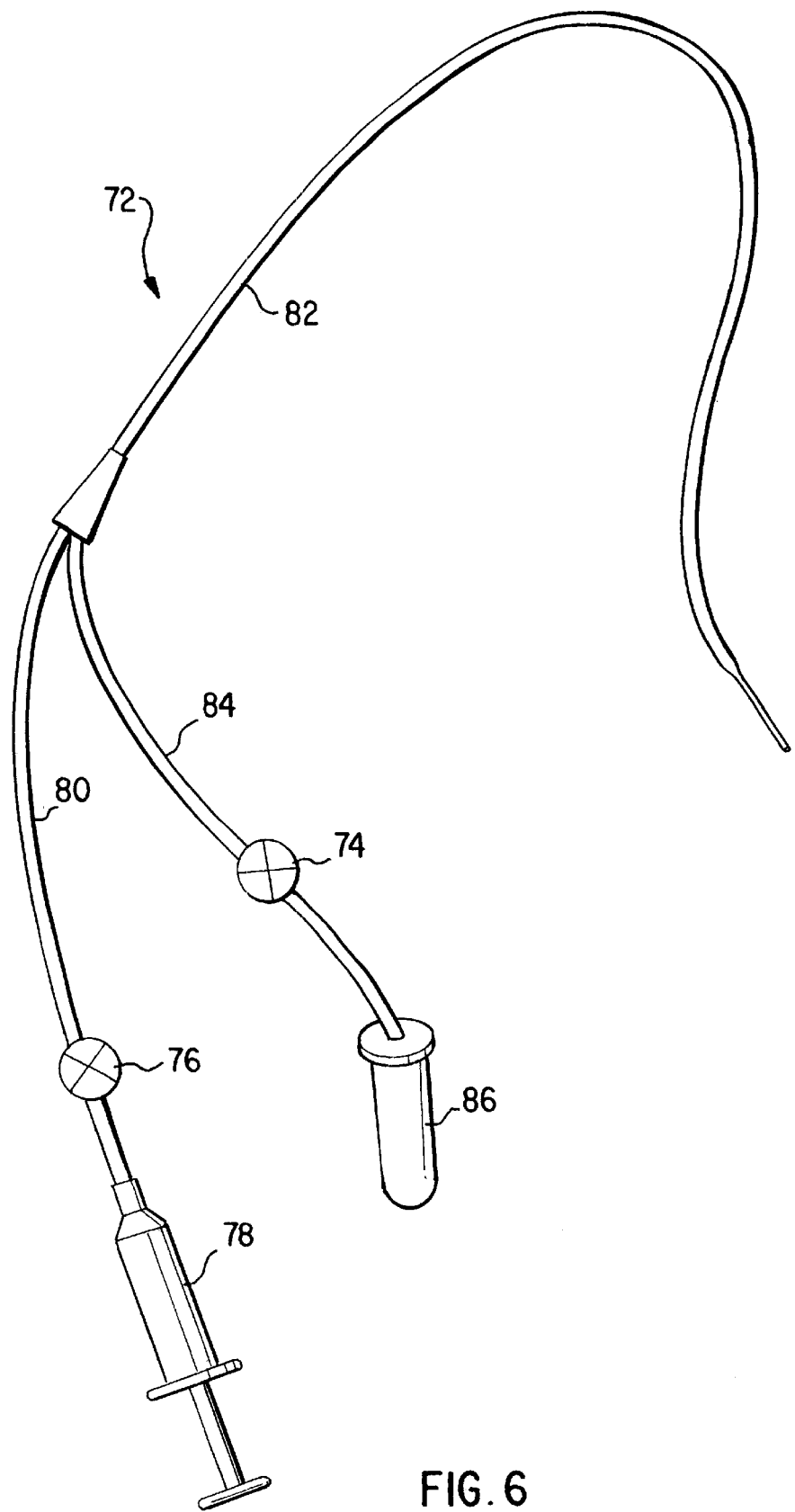
FIG. 6 depicts a single or double lumen catheter having an infusion and collection lumen outside the catheter with stopcocks on each external lumen to control fluid flow into or out of each lumen.
Figure 7:
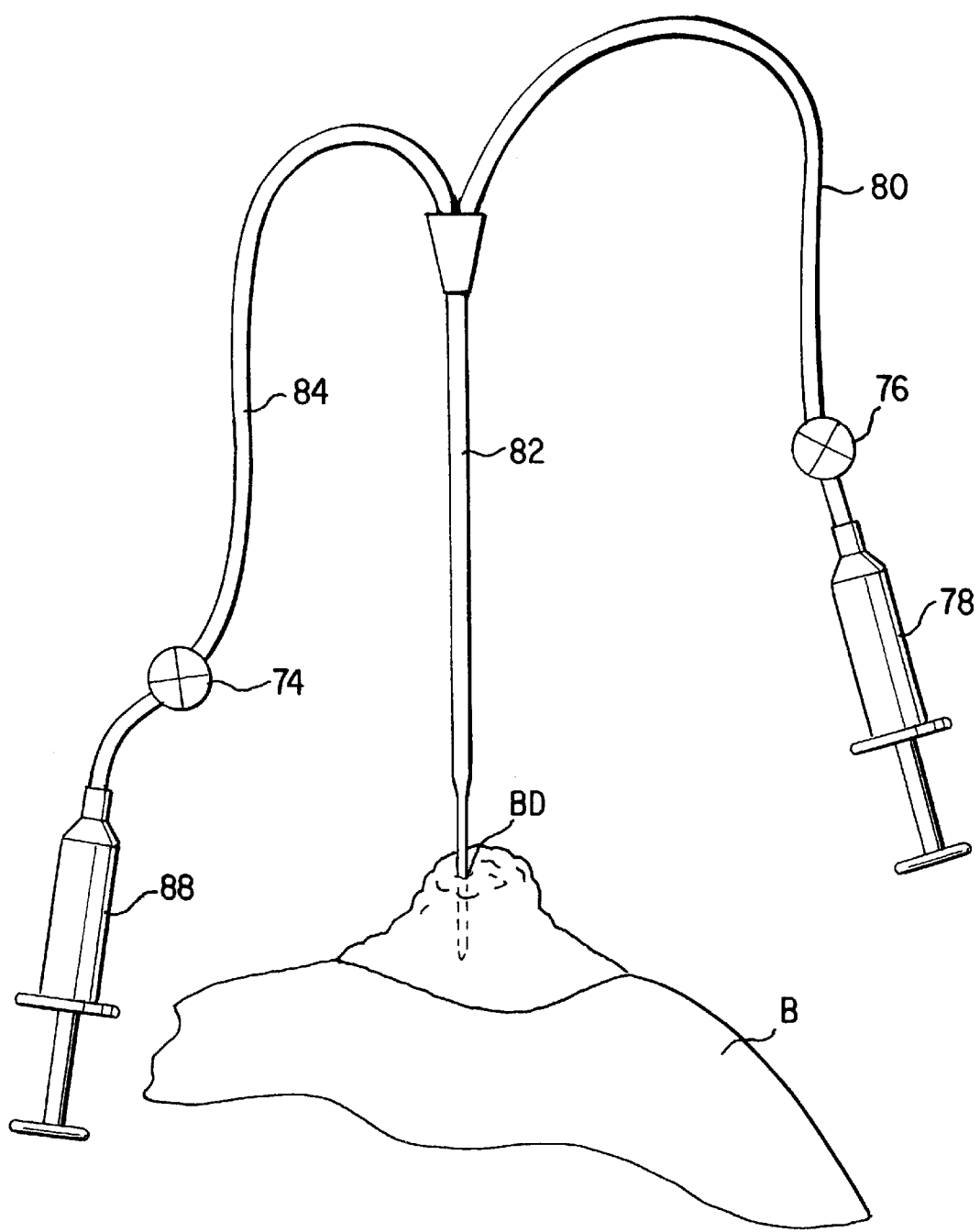
FIG. 7 illustrates a breast duct accessed by a single or double lumen catheter having separate infusion and collection lumens outside the ductal access portion of the catheter, having also stop cocks on each external lumen for controlling fluid flow in the lumen, and having an infusion receptacle on the infusion lumen and a collection receptacle on the collection lumen.

FIG. 6 depicts an alternative ductal access device 72 with stop cocks 74 and 76 to control the fluid flow into and out from an accessed duct. A syringe 78 for infusing fluid into the duct is connected to one arm 80 of an access tube 82. A collection tube 86 is connected to another arm 84 connected to the access tube 82. The access tube may have single, dual, or multiple lumens as described elsewhere herein. FIG. 7 depicts the device of FIG. 6 accessing a breast duct BD. Fluid may be infused from syringe 78 with stopcock 76 open and stopcock 74 closed. After infusing a desired volume as set forth above, and optionally massaging the breast, stopcock 74 may be opened and fluid collected in passive receptacle 86 (FIG. 6) or actively withdrawn using a second syringe 88 to apply a vacuum through the collection arm 84.

FIGS. 8 and 8A–8C illustrate a dual lumen catheter 100 having lumens 102 and 104 that access the breast duct. A reduced diameter region 106 accesses the breast duct and the catheter resides in the duct at a depth of about 3.5 cm. The reduced diameter portion 106 of the catheter has three lumens 103, 105, and a third central lumen which receives a fixed stiffening wire 108 (FIG. 8B). The proximal part of the catheter 100 that does not access the breast duct is depicted in cross section in FIG. 8A having interior lumen 104 and an annular lumen 102 both which provide fluid flow (either collection or infusion) during use of the catheter to retrieve cellular material from the breast duct. Proximal connector 110 is near a proximal end of the proximal portion and branches into an infusion arm 112 and aspiration arm 114, each connected to one of the lumens 102 and 109. The distal portion 106 and proximal portion meet at shoulder 116 where the lumens 102 and 104 make a transition to annular lumens 103 and 105 (FIG. 8B). Distal tip 120 may be atraumatic for entry into a ductal orifice and ductal lumen. Usually, side ports 122 will be formed on the distal section 106 to permit fluid inflow and outflow from the lumens 103 and 105, respectively.

Figure 9A:
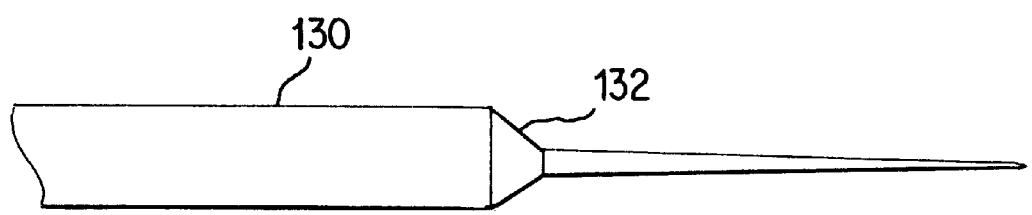
FIGS. 9A and 9B depict alternative transition zones in a ductal access catheter.
Figure 9B:
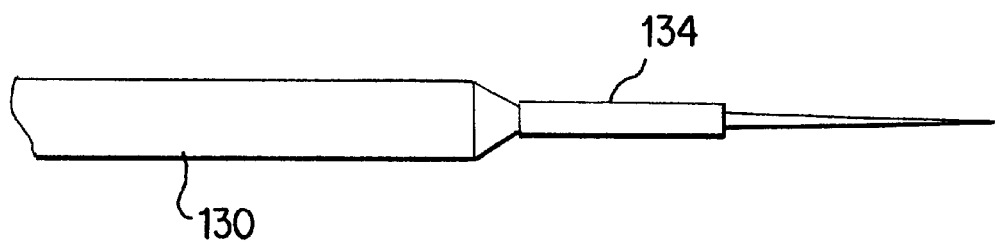

FIGS. 9A and 9B depict two formats of transition between a distal end of an access tube 130 which accesses the breast duct and the proximal end which resides outside the breast duct. Shoulder 132 in FIG. 9A has a graduated transition, and shoulder 134 in FIG. 9B has a stepped transition.

Figure 5:
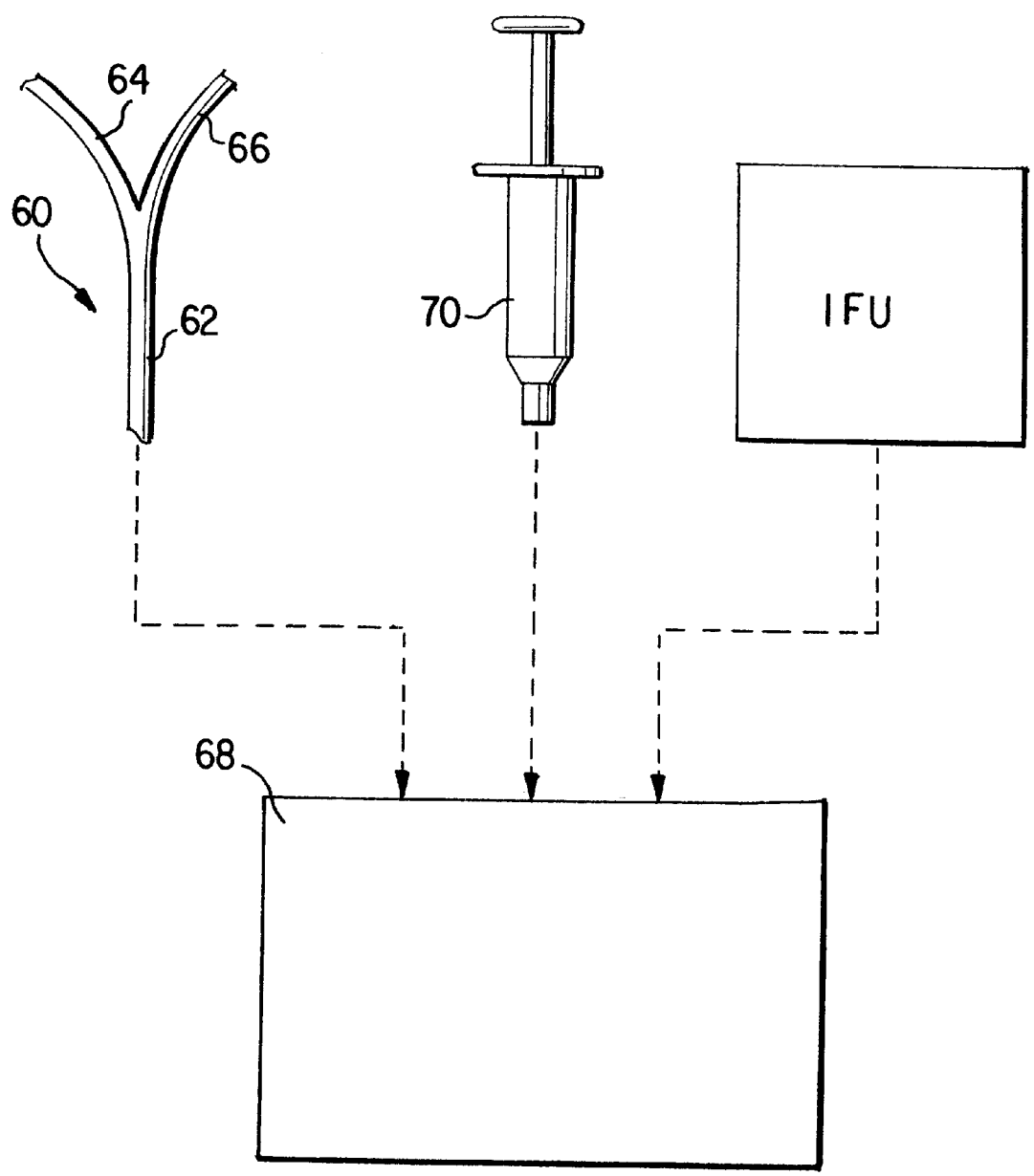
FIG. 5 depicts a kit comprising a single lumen catheter having infusion and collection lumens outside the ductal access portion of the catheter, a premeasured solution to infuse into the duct and instructions for use of the catheter and wash fluid to access a breast duct and retrieve cellular material.

The invention also provides systems and kits 60 for collecting cellular material from a breast duct. FIG. 5 depicts a system comprising an access device 62, such as a single lumen catheter having infusion and collection arms 64 and 66 outside the ductal access portion of the catheter, optionally a premeasured solution to infuse into the duct and instructions for use of the catheter and wash fluid to access a breast duct and retrieve cellular material, e.g., contained in syringe 70. The system 60 includes a container 68 and instructions setting forth any of the methods described herein, such as the method for obtaining cellular material from a human breast milk duct comprising introducing a ductal access device having at least one lumen therethrough into a duct, introducing a wash fluid through the access device lumen into the milk duct, wherein a volume of at least 2 ml is present within the duct for a preselected time; and collecting at least a portion of the wash fluid from the duct through the lumen of the access device. Wash fluid can be included in the kit and can comprise for example, saline, phosphate buffered saline, a nonabsorbable fluid, an isotonic solution, an osmotic solution, a hypotonic solution, a hypertonic solution, a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, or albumin.

Other ductal access systems available comprise a ductal access device as a container holding a premeasured volume of ductal wash fluid. The ductal access device comprises an access tube having a distal end, at least one lumen therethrough, and dimensions which permit introduction of the distal end through a ductal orifice and positioning a distal end thereof distal to the ductal sphincter of a human breast. The device may also comprise a means on the access tube for positioning the distal end distal to the ductal sphincter. The container can comprise a syringe for connection to the first side port. The pre-measured volume is in the range from 2 ml to 100 ml. The wash fluid can comprise for example, saline, phosphate buffered saline, a nonabsorbable fluid, an isotonic solution, an osmotic solution, a hypotonic solution, a hypertonic solution.a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, or albumin.

Another ductal access system comprises a ductal access device comprising an access tube having a distal end, a single lumen therethrough, and dimensions which permit introduction of the distal end through a ductal orifice and positioning a distal end thereof distal to the ductal sphincter, an infusion connector providing a fluid flow path into the lumen of the access tube; and a collection connector providing a fluid outlet path from the lumen of the access tube, said infusion and collection connectors being isolated from each other so that fluid may be infused through the infusion connector and simultaneously removed through the collection connector, the system also including a container holding a premeasured volume of ductal wash fluid. The container can comprise a syringe for connection to the first side port, and the premeasured volume can be in the range from 2 ml to 100 ml. The fluid can comprise saline, phosphate buffered saline, a nonabsorbable fluid, an isotonic solution, an osmotic solution, a hypotonic solution, a hypertonic solution, a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, or albumin.

Another ductal access system can comprise a ductal access device comprising a hub having an internal elongate manifold, a lower port at a bottom of the manifold, and first and second side ports spaced above the lower port; and an access tube having a distal end, a proximal end, a lumen therethrough, and dimensions which permit introduction of the distal end through a ductal orifice and a positioning a distal end thereof distal to the ductal sphincter of the human breast, wherein the proximal end of the tube is attached to the lower port of the hub, the ductal access system comprising also a container holding a premeasured volume of ductal wash fluid. The container can comprise a syringe for connection to the first side port. The pre-measured volume is in the range from 2 ml to 100 ml. The ductal access fluid can comprise, e.g., saline, phosphate buffered saline, a nonabsorbable fluid, an isotonic solution, an osmotic solution, a hypotonic solution, a hypertonic solution, a protein, a colloid, a sugar, a polymer, mannitol, sorbitol, glucose, glycerol, sucrose, raffinose, fructose, lactulose, sodium chloride, polyethyleneglycol (PEG), maltodextrin, dextran (e.g. dextran 70), hydroxyethyl starch, fluid gelatin, a synthetic colloid, an antibody, a binding protein, or albumin.

Additionally, a ductal access system is provided comprising a ductal access catheter comprising a catheter body having a distal end and a proximal end and including at least a distal portion and a proximal portion, wherein the distal portion has a cross-sectional geometry which can be inserted through a ductal orifice into a ductal lumen of a human breast, wherein the proximal portion has a cross-sectional geometry which inhibits insertion through the ductal orifice and into the ductal lumen; and wherein the catheter body has at least an infusion lumen and an collection lumen each of which has a distal port near a distal end of the distal portion and a proximal connector near a proximal end of the proximal portion, the ductal access system comprising also instructions for use setting forth a method for lavage of a ductal network in a human breast including introducing a wash fluid through the infusion lumen into the ductal network and withdrawing the wash fluid and substances borne by the wash fluid from the ductal network through the collection lumen.

At least one of the lumens of the breast duct access device can have a means to control the fluid flow through that lumen. The inflow lumen can be connected to a syringe or other infusion mechanism for infusing lavage fluid into the breast duct. The outflow lumen can be connected to a collection tube, a collection syringe, or other collection means for collecting the lavage fluid after it has mixed with the ductal fluid in the breast duct. The means to control the fluid flow in a lumen can be, e.g. a stopcock, valve or other control unit that is capable of closing or opening a port of the lumen. The lumens themselves may be compressible or pinchable with fingers or clamps or other pinching or compressing mechanism. A stopcock may be attached at a lumen of a dual lumen catheter to control the fluid flow through that lumen. An inflow lumen may have an inflow stop cock to control fluid flow through an inflow port. An outflow lumen may have an outflow stop cock to control fluid flow through an outflow port. The device can have stopcocks (or other means to control fluid flow) on both an inflow and an outflow lumen. These control units, valves or stopcocks are capable of operating separately, e.g. so that when an inflow port is opened, an outflow port can be closed, etc. Thus, patterns of control of the fluid flow in a lavage procedure of a breast duct can include, e.g. an open inflow when an outflow is closed, an open inflow when an outflow is opened, a closed inflow when an outflow is opened, and a closed inflow when an outflow is closed. The catheter may have the graduated duct probe attached to it at the distal end for accessing the duct. Where the probe is unattached to the catheter, and is used for dilating the orifice, the catheter can have a tip appropriate for accessing the dilated duct upon removal of the probe.

Lavage fluid can be a saline solution, e.g. normal saline, or phosphate buffered saline (PBS), or other fluid capable and suitable for washing a body duct. The lavage fluid will generally be biocompatible and nontoxic to the patient. The lavage fluid can further comprise additives, e.g. gas, particles or other fluids. These additives to the lavage fluid may have various purposes, however, during a lavage procedure, the preeminent purpose will generally be to increase a recovery of fluid and/or cellular material, and/or molecular species from the ducts. Thus, such gas may provide a cleansing action on the ductal walls for example, encouraging ductal epithelial cells located e.g. in a lesion in the duct to shed and be retrievable during the lavage procedure. Similarly, particle additives may serve to encourage fluids, cellular material and/or molecular species to follow the particles in the flow of lavage fluid through the ducts and be retrieved in the lavage procedure. Such additives as detergents, e.g. agents tending to form micelles for collecting ductal contents including cells and molecular species may provide additional yields of cells, molecular species and fluids in a lavage procedure. The gas can be ambient air or a related product, and the lavage fluid can comprise the air mixed in with the fluid for delivery into the duct. The presence of air or other gas may serve to increase the retrieval of cells and fluid as compared to a procedure conducted using lavage fluid alone. The air can be bubbled into the fluid, or introduced into the fluid mixture by other standard means. The air may also be mixed into the lavage fluid as the lavage fluid is delivered into the duct, e.g. where the infusion port allows for delivery of both air and lavage fluid into the inflow lumens where the two mix and both are delivered to the accessed ducts.

The lavage fluid can further contain other agents that may aid in the retrieval of fluid or cells or both from the duct or may serve some other useful purpose in the procedure. For example, the lavage fluid may include or be preceded by or followed by such other agents that may aid in the retrieval of fluid or cells or both from the duct, or may serve some other useful purpose in the procedure. Such other agents can be, for example, an oncotic and/or osmotic agent capable of increasing the amount of collectable fluid in the ductal lumen, or a detergent that can help wash out more cells, or an agent that may help detach more cells from the duct wall into the ductal lumen (e.g. trypsin, collagenase, or EDTA). The agent can be an oncotic agent and/or an osmotic agent or both. Oncotic and osmotic agents are agents that retain fluid around them or draw fluid to them. The agent can be soluble, e.g. soluble in a suitable solvent, including e.g. water, buffered water, or a saline solution. Preferably the solvent is biologically compatible with mammals. Suitable solvents will be those that both effectively dissolve the agent and are not toxic to a mammal. The agent can be a molecular species including e.g. a protein, colloid, sugar, or polymer. The agent can be mannitol, sorbitol, glucose, glycerol, sucrose, raffinose, fructose, lactulose, sodium chloride, albumin, polyethyleneglycol (PEG), maltodextrin, dextran (e.g. dextran 70), hydroxyethyl starch, fluid gelatin, or a synthetic colloid. Agents including e.g. mannitol, sorbitol, PEG, glycerol are described in THE MERCK INDEX, $12^{th}$ ed. 1996, Whitehouse Station, N.J. Others, including maltodextrin, dextran and others are available from Aldrich Chemical Co. in Milwaukee, Wis. or Sigma Chemical Co. in St. Louis, Mo. The molecular weight of a suitable oncotic agent can be determined as optimally within the range of the molecular weights of suitable oncotic agents available.

Where the agent in the lavage fluid is a protein, the protein can be a binding protein or an antibody. The binding protein can be albumin. The antibody can be capable of binding an epitope found in a breast duct, e.g. an epithelial cell surface marker or cancer cell marker, etc. Where the agent is a protein, the protein is of a molecular weight in the neighborhood of albumin or higher, so that it is capable of acting as an oncotic agent in the lumen of the milk duct. Suitable antibodies are commercially available. Also the agent can be a mixture of osmotic and/or an oncotic agents. The oncotic agent and/or osmotic agent can comprise a mixture of any two or more osmotic and/or oncotic agents, e.g. mannitol, sorbitol, glucose, glycerol, sucrose, raffinose, fructose, lactulose, sodium chloride, albumin, polyethyleneglycol (PEG), maltodextrin, dextran (e.g. dextran 70), hydroxyethyl starch, fluid gelatin, an antibody or a synthetic colloid. Preferably the agent is not toxic to a mammal, particularly not toxic to a human. The agent can be an agent not capable of freely diffusing into or beyond the cells that line the milk ducts of the breast. The agent can also be an agent not capable of absorption into the cells within the duct. For example, the agent can have a molecular weight large enough to make absorption or diffusion into the breast duct lining, cells or interstitial space beyond the lining improbable.

The method provides that the catheter is used to access the breast duct after being primed (i.e. filled) with lavage fluid with both outflow and inflow ports closed. The outflow stop cock can be opened and the fluid allowed to infuse into the duct from the outflow to flush the outflow port at the catheter tip and make it ready to receive the ductal fluid and wash fluid into the outflow lumen during the lavage procedure. The outflow port at the stopcock is then closed by closing the outflow stopcock. The inflow port is opened by opening the inflow stopcock. Wash fluid is infused into the breast duct until resistance is met. The amount of this first infusion bolus will vary depending on the size of the breast duct being infused. The inflow port is then closed by closing the inflow stopcock. The breast is massaged by applying manual external pressure on the breast tissue. The outflow lumen is opened and the breast is massage and squeezed and fluid is collected in the collection receptacle attached to the outflow lumen. The process can be repeated several times. Subsequent to the first larger bolus of wash fluid, lesser amounts of wash fluid can be infused into the duct and collected in the outflow collection receptacle as just described.

A practitioner desirous of increasing a yield of fluid and cells from a lavage of a patient's breast ducts, and/or desirous of retrieving fluid and cells from distal regions of the ductal architecture, can massage the breast of the patient once the fluid has been infused into the duct. The fluid is infused into the duct (with the outflow port closed) to a point of resistance and then the inflow port is closed. The breast can be massaged at this point to effect a mixing of the ductal fluid with the lavage fluid, and to generally provide some gentle disruption of ductal cells in the duct and allow them to enter the fluid mix. The outflow port can be opened at this point, and allow the massaging to continue, it can be supplemented with a squeezing or compressing of the breast, i.e. from the base of the breast upwards towards the nipple in order to encourage as much fluid to escape via the outflow lumen and into the collection receptacle.

Modifications to the method of lavage can include that the patient is seated during the lavage procedure, rather than the standard or classic supine (face up) position. In addition, the patient may be lavaged in a prone position, face down, with nipples and breast down. The prone face down position takes advantage of gravity and allows the breast ducts to drain into the collection receptacle during the procedure when the outflow port is open. Thus, the lavaging procedure can include infusing the breast duct with a wash fluid through an open inflow lumen while an outflow lumen is closed; closing the inflow lumen when the duct is filled; squeezing or massaging the breast or both; and opening the outflow lumen to collect the wash fluid.

The cells collected can comprise ductal epithelial cells; the ductal fluid collected can comprise molecular and cellular material. Analysis of the ductal epithelial cells and/or the molecular and cellular material in the ductal fluid can proceed as described below discussing the diagnostic methods possible of these collected materials. The collected cells and fluid and fluid components can be analyzed, e.g. as described or suggested herein. The lavage fluid including the ductal cells can be analyzed for diagnostic purposes. Conditions in a breast milk duct that are desirable to diagnose include a cancer or precancer condition. The precancer condition can include atypical ductal hyperplasia (ADH) or low grade ductal carcinoma in situ (LG-DCIS). The diagnostic agent may also have the ability to diagnose other breast related conditions, including, e.g. fibrotic, cystic or conditions relating to lactation. Diagnostic agents can be mixed with the ductal fluid (either in the lavage procedure, or after the fluid is collected).

The diagnostic agents can include tags for detecting lesions or other abnormalities or characteristic anatomical or molecular identities in the breast ducts, including e.g. chemical tags or antibodies. The tags may provide the capacity for visualizing the location of a lesion, including, e.g. fluorescent tags, or biotinylated tags. Antibodies can also be tagged so that the binding antibody is identifiable. Antibodies can be whole antibodies, or parts of antibodies including, e.g. Fab fragments, heavy and/or light chain fragments, single chain antibodies and other modified antibodies commonly known about and used in the field of antibody-assisted diagnosis. Diagnostic antibodies or other tags can be to a number of markers, including e.g. the following cancer markers that are exemplary and may be used to analyze the breast duct condition. Standard assay procedures for identifying the markers can be used. analyzed for the presence of soluble factors or other components that might indicate the presence of cancerous or precancerous ductal epithelial cells in the duct. The epithelial cells retrieved from the breast duct can be analyzed for protein markers, nucleic acid markers, chromosomal abnormalities, or other characteristic changes that would signal the presence of cancerous or precancerous cells. In addition, other cells found in the duct can also be analyzed, e.g. for an increase or decrease in these cells as compared to normal ductal fluid, or for qualities of these cells themselves. Thus, the condition of the breast duct can be analyzed e.g. for soluble protein content or presence of other ductal fluid components, including also secreted products of ductal epithelial cells) or the ductal epithelial cells themselves can be analyzed, for example, for cell morphology, for protein markers, for nucleic acid markers, and for biochemical markers.

In addition, any of the cells of the duct can be analyzed for morphological abnormalities in cell components, including, e.g. morphological abnormalities of the nucleus, cytoplasm, Golgi apparatus or other parts of a cell. The cells can be analyzed for whether they do or don't aggregate (e.g. in clumps) or by making comparisons of the ductal epithelial cells with other cell types retrieved in the ductal fluid (e.g. macrophages, lymphocytes, foam cells and other possible components of ductal fluid). The ductal epithelial cells can be analyzed for their molecular contents or the morphology of the ductal epithelial cells, including, e.g. protein markers, nucleic acid markers, biochemical markers in the cells or on the cell surfaces or for any evidence of neoplasia.

In addition to some markers discussed and/or articles or books cited on breast cancer and breast precancer markers, including markers listed in Porter-Jordan and Lippman, "Overview of the biological markers of breast cancer", Hematology/Oncology Clinics of North America vol. 8 (1):73–100, 1994, the following cancer markers are listed here as exemplary and may be used as well as other markers to analyze the condition of a breast duct, including analysis of the ductal contents (including fluid and cells). Standard assay procedures for identifying the markers can be used, including antibodies or other binding partners, labels, stains, pattern analysis (for cells and cell components), and in general any other chemical or visual identification techniques.

Markers that are presently being studied by researchers presently include, carcinoma embryonic antigen (CEA), prostate specific antigen (PSA) Erb B2 antigen, gross cystic disease fluid protein-15 (GCDFP-15), and lactose dehydrogenase (LDH). For CEA see Imayama et al, *Cancer* 1996, 78(6):1229–34; Inaji et al, *Cancer* 1987,60(12):3008–13; Mori *Int Conger Seer* 1989, 807:211–8; Inaji, et al, *An To Kagaku Ryoho* 1991, 18(2):313–7; Yayoi, et al *Gan To Kagaku Ryoho* 1994, 21 Suppl 2:133–9; Mori, et al *Jpn J Clin Oncol* 1989,19(4):373–9; Foretova, et al *Proc Annu Meet Am Soc Clin Oncol* 1995,14:A101; and Nishiguchi, et al *Rinsho Byori* 1992,40(1):67–72. For PSA see Foretova, Garber Lancet 1996,347(9015):1631; Sauter et al, *Cancer Epidemiology, Biomarkers & Prevention.* 5(12):967–70, 1996; Sauter and Daly (1996) *Proc Annu Meet Am Assoc Cancer Res* 37:A1458; and Foretova and Garber (1996) *Proc Annu Meet Am Assoc Cancer Res* 37:A1446. For Erb B2 see Motomura (1995) *Breast Cancer Res and Treat* 33:89–92; and Inaji et al (1993) *Tumour Biol* 14: 271–8. For GCDFP-15 see Petrakis et al (1994) *Proc Annu Meet Am Assoc Cancer Res* 35:A1698. For LDH see Mannello et al (1995) *Cancer* 76:152–4; and Kawamoto (1994) *Cancer* 73:1836–41.

Chromosomal abnormalities in ductal epithelial cells can also provide information and act as a marker to identify cancer or precancer as described in Mark et al (1999) *Cancer Genet Cytogenet* 108:26–31; Lundlin and Mertens (1998) *Breast Cancer Res Treat* 51:1–15; Newsham (1998) *Am J Pathol* 153:5–9; Larson et al (1998) *Am J Pathol* 152:1591–8; Adelaide et al (1998) *Genes Chromosomes Cancer* 22:186–99; Fejzo et al (1998) *Gene Chromosome Cancer* 22:105–113; Dietrich et al (1998) *Hum Pathol* 12: 1379–82; Cavalli et al (1997) *Hereditas* 126:261–8; Adeyinka et al (1997) *Cancer Genet Cytogenet* 97:119–21; Afify and Mark (1997) *Cancer Genet Cytogenet* 97:101–5; Brenner and Aldaz (1997) *Prog Clin Biol Res* 396: 63–82; Mark et al (1997) *Ann Clin Lab Sci* 27:47–56; and Fabian et al 1993 *J. Cellular Biochemistry* 17G:153–16.

In addition, exemplary markers are described in Masood, (Prediction of recurrence for advanced breast cancer. Traditional and contemporary pathologic and molecular markers) *Surgical Oncology Clinics of North America.* 4(4): 601–32, 1995; Lopez-Guerrero et al (1999) *J Hematother* 8(1):53–61; Marjumdar and Diamandis (1999) *Br J Cancer* 79(9–10):1594–602; Balleine et al (1999) *Br J Cancer* 79 (9–10):1564–71; Houston et al (1999) *Br J Cancer* 79(7–8): 1220–6; Nikolic-Vukosavljevic et al (1998) *Tumori* 84(6): 691–4; Maguire et al (1998) *Int J Biol Markers* 13(3): 139–44; Stearns et al (1998) *Breast Cancer Res Treat* 52(1–3):239–59; Eiriksdottir et al (1998) *Eur J Cancer* 34(13):2076–81, and U.S. Pat. No. 5,169,774. Many known breast cancer markers are discussed and described in readily available medical textbooks on breast cancer. Other markers are also listed herein.

The morphology of the cells or cellular contents retrieved in the ductal fluid and wash fluid may also be examined. The cellular contents can include, e.g. protein, nucleic acid, or other molecular markers in the cells. Cell morphology can serve to establish whether the ductal epithelial cells are normal (i.e. not precancerous or cancerous or having another noncancerous abnormality), precancerous (i.e. comprising hyperplasia, atypical ductal hyperplasia (ADH) or low grade ductal carcinoma in situ (LG-DCIS)) or cancerous (i.e. comprising high grade ductal carcinoma in situ (HG-DCIS), or invasive carcinoma). Analysis of cell contents may serve to establish similar staging as established by morphology, capturing generally a progression of a precancerous or cancerous condition in the cells.

Administering fluid to the ductal lumen for the purpose of collecting that fluid mixed with the fluid from the duct is complicated by the fact that absorbable wash fluids are partly absorbed into the breast from the duct. Thus, the fluid retrieved is less than that infused, even considering that it includes the ductal fluid that was residing in the duct. Administering an agent in the wash fluid that is capable of increasing or maintaining the fluid volume in the duct is a great advantage to the process. Thus, the invention provides administering a nonabsorbable fluid or a fluid that actually draws fluid to it, e.g. an oncotic or osmotic fluid in the process of collecting fluid from the duct. Administering the nonabsorbable fluid has the advantage also of providing the practitioner with a way to monitor or standardize the ductal fluid and cellular return in any given volume of fluid infused and retrieved. For example 10 ml of the nonabsorbable fluid is administered to the duct, and 9.5 ml of that fluid is collected. Maybe 100 epithelial clusters are contained in the fluid collected. This information can be noted, and during future procedures on that same duct can be compared. The advantage of using a nonabsorbable is that the ductal fluid yield may be increased with the retrieval of most or all of the infused fluid, and the practioner will be able to keep track of the amount infused versus the amount collected.

A nonabsorbable fluid can be used in order to provide a standardization to the process so that the amount infused can be correlated with the amount collected, knowing that since the fluid cannot be absorbed in the duct, and collecting of all or most of the fluid that is infused is possible.

Identification of the location of the ducts prior to accessing them can be made as described in PCT application to the Regents of the University of California at Los Angeles filed Sep. 15, 1998 to Barsky et al entitled "Methods and Kits for Identifying Ductal Orifices in a Nipple", or U.S. Ser. No. 09/153,564 filed Sep. 15, 1998 to Barsky et al.

The agent is an agent capable of in effect increasing the amount of collectable fluid in the ductal lumen. Thus the agent can be a nonabsorbable agent or fluid or an oncotic agent and/or an osmotic agent or a combination of two or all three. Oncotic and osmotic agents are agents that retain fluid around them or draw fluid to them. The agent can be soluble, e.g. soluble in a suitable solvent, including e.g. water, buffered water, or a saline solution. Preferably the solvent is biologically compatible with mammals. Suitable solvents will be those that both effectively dissolve the agent and are not toxic to a mammal.

The agent can be a molecule including e.g. a protein, colloid, sugar, or polymer. The agent can be mannitol, sorbitol, glucose, glycerol, sucrose, raffinose, fructose, lactulose, sodium chloride, albumin, polyethyleneglycol (PEG), maltodextrin, dextran (e.g. dextran 70), hydroxyethyl starch, fluid gelatin, or a synthetic colloid. Agents including e.g. mannitol, sorbitol, PEG, glycerol are described in THE MERCK INDEX, $12^{th}$ed. 1996, Whitehouse Station, N.J. Others, including maltodextrin, dextran and others are available from Aldrich Chemical Co. in Milwaukee, Wis. or Sigma Chemical Co. in St. Louis, Mo. The molecular weight of a suitable oncotic agent can be determined as optimally within the range of the molecular weights of suitable oncotic agents available.

Where the agent is a protein, the protein can be a binding protein or an antibody. The binding protein can be albumin. The antibody can be capable of binding an epitope found in a breast duct, e.g. an epithelial cell surface marker or cancer cell marker, etc. Where the agent is a protein, the protein is of a molecular weight in the neighborhood of albumin or higher, so that it is capable of acting as an oncotic agent in the lumen of the milk duct. Suitable antibodies are commercially available.

Also the agent can be a mixture of osmotic and/or an oncotic agents. The oncotic agent and/or osmotic agent can comprise a mixture of any two or more osmotic and/or oncotic agents, e.g. mannitol, sorbitol, glucose, glycerol, sucrose, raffinose, fructose, lactulose, sodium chloride, albumin, polyethyleneglycol (PEG), maltodextrin, dextran (e.g. dextran 70), hydroxyethyl starch, fluid gelatin, an antibody or a synthetic colloid.

The agent can be an agent not capable of freely diffusing into or beyond the cells that line the milk ducts of the breast. The agent can also be an agent not capable of absorption into the cells within the duct. For example, the agent can have a molecular weight large enough to make absorption or diffusion into the breast duct lining, cells or interstitial space beyond the lining improbable.

Whether an agent is capable of increasing or at least maintaining the amount of collectable fluid (with relation to the amount of fluid infused) in the ductal lumen can be determined by experimentation to identify whether collectable fluid in the duct is increased upon administration of an agent as compared to administration of a control isotonic solution to a neighboring control duct. Likewise the best volume and concentration of the agent can be determined by a comparison of the amount of collectable fluid yielded with a change in a variable such as a volume or concentration of agent administered. The agents including nonabsorbable fluid and/or oncotic and/or osmotic agents to be tested can be delivered to the duct of a human, rat, rabbit, pig or other appropriate mammal, and the ductal fluid can be collected. Where the fluid yield is greater than control fluid collected from a neighboring duct (after injection of a control solution, preferably of equal volume as the tested solution), that agent is suitable for use in the method. The increased fluid amount should be at least 50% and more preferably close to 100% of an increase of fluid collectable from the ducts that are compared. In the case where the practitioner seeks to increase the amount of fluid collected from the amount infused, the fluid yield from the duct administered with the agent being tested can be several fold that of the control fluid yield. Where the goal is merely to provide for a collection fluid amount that is close to the amount infused, the parameters for success are that the amount of fluid collected from the duct after infusion of a set aliquot of fluid is closer to the amount infused that would have been possible if the infusion fluid had been an absorbable fluid such as saline. Such a comparison can be tested by doing a control infusion and collection in a duct using e.g. saline and then repeating the procedure in the same duct using a nonabsorbable fluid, e.g. a PEG containing fluid or the like.

The appropriate concentration and volume of oncotic agent and/or osmotic agent in solution injected into a duct can be determined by routine experimentation including cannulation or catheterization of mammalian nipples (e.g. rat, rabbit, pig or human nipples) to determine at which concentration and volume the agent in solution yields the most volume of fluid collectable from the duct as compared to the fluid collectable from a control duct. Experiments can be designed for testing a variety of oncotic and/or osmotic agents, concentrations, volumes, and mixtures of agents in all varieties of mammals having breast ducts.

Fluid collected from the milk ducts, can include constituents of biological fluids, e.g. those typically found in breast duct fluid, e.g. water, cells, cellular markers, molecular markers, nucleic acids, proteins, cellular debris, salts, or organic molecules. These constituents can be analyzed by any appropriate method depending on the practitioner's purposes in obtaining the fluid.

The fluid can comprise cells including e.g. epithelial cells and abnormal cells. The cells can be analyzed for cellular, protein, nucleic acid, or other molecular markers or for shape or other abnormalities. Analysis of the cells can provide diagnostic or prognostic information for an evaluation of the condition of the breast or breast ducts. Removal of cells can be conducted in the presence of the agent, and preferably the action of the osmotic and/or oncotic agent provides for removing cells that can be analyzed.

The invention includes a kit for increasing the amount of fluid collectable from a milk duct of a breast comprising a nonabsorbable agent and/or an osmotic agent and/or an oncotic agent, a medical tool for delivering the agent to the ductal lumen, and instructions for use. The nonabsorbable agent and/or oncotic and/or osmotic agent can be those described herein or other comprising like properties and/or functions in a breast duct. The medical tool can be any tool that enables delivery of such agent. The instructions can direct a protocol for administration including how to administer the agent, how much time to wait before collecting the fluid, how to collect the fluid, and how to analyze the fluid collected.

The retrieved fluid can comprise constituents of the breast milk duct fluid, e.g. including water, cells, cellular markers, molecular markers, nucleic acids, proteins, cellular debris, salts, or organic molecules. Analyses can be made that identify molecular or cellular markers, cellular characteristics, e.g. by cytology, and for making any other assessment of any of the constituents of the fluid. Cells that are retrieved and analyzed can be epithelial cells or abnormal cells.

Multiple lumen ductal access catheters, having more than one lumen in the access portion of the catheter, according to the present invention will comprise a catheter body having a distal end and a proximal end and including at least a distal portion and a proximal portion. The catheter will have at least two continuous lumens extending through both the proximal and distal portions. The lumens can be fluid carrying, and fluid can pass from the proximal portion to the distal portion of one lumen and from the distal portion to the proximal portion of a second lumen. The distal portion has a cross-sectional geometry which can be inserted through a ductal orifice into a ductal lumen of a human breast for the purpose of ravaging the breast duct. The proximal portion has a cross-sectional geometry which inhibits insertion through the ductal orifice and into the ductal lumen thereby placing limits on the extent that the catheter penetrates the breast duct during the lavage procedure. The lumens of the catheter are an infusion lumen and an aspiration or collection lumen. Each lumen has a distal port near the distal end of the distal portion of the catheter. One distal port is for infusing liquid into the duct (a port on the infusion lumen). The other distal port is for aspirating or collecting fluid from the duct (a port on the aspiration lumen). The catheters also have a proximal connector near a proximal end of the proximal portion for connecting e.g. to a fluid receptacle that holds fluid for infusion into the duct (e.g. a wash or lavage fluid) and for connecting to a collection receptacle for collecting the contents of the duct that are aspirated in the aspiration lumen (e.g. a syringe that can both aspirate and collect the ductal fluid and/or ductal contents).

The ductal access catheter will have a total length in the range of from about 2-cm to about 60-cm, usually about 30 cm to about 45-cm. The length of the proximal portion will typically be in the range of about 15-cm to about 50 cm, more typically in the range from about 30 cm to about 40 cm. The distal portion will typically be in the range from about 2.5-cm to about 8 cm, more typically in the range from about 3.0 cm to about 5.5 cm.

The proximal and distal portions will preferably be joined to each other with an intermediate zone between them to accommodate the difference in cross-sectional geometry between the proximal and distal portions. The intermediate zone can be a stepped decrease in cross-sectional geometry from proximal to distal portions, or may be a gradual decrease in cross-sectional geometry from proximal to distal portions. The body segments can be joined in any conventional manner to each other (and/or to the either end of the element creating the intermediate zone) including methods such as heat fusion, adhesive bonding, coextrusion, or the like. In the exemplary embodiment, the distal and proximal portions will be coextruded and the coextrusion process will generate the intermediate zone in accommodating the differential cross-sectional geometry of the proximal to the distal portions.

The catheter can have the distal portion of the catheter body stiffened over at least a part of its length to facilitate insertion through the ductal orifice and into the ductal lumen. The stiffening effect can be created by insertion of a third lumen in the distal portion, the third lumen comprising a wire. The wire can be made of some relatively stiff metal, e.g. tungsten or steel. The stiffened distal portion of the catheter body can have an average bending stiffness in the range from about 0.010 inch-lbs to about 0.5 inch-lbs. Typically the bending stiffness of the distal portion will be about 0.105 inch-lbs.

The catheter may be composed of any biologically compatible polymeric resins or metal having suitable characteristics when formed into the tubular catheter portions. Exemplary materials include polyvinyl chloride, polyethers, polyamides, polyethylenes, polycarbonate, polyurethanes, copolymers thereof and the like. The distal portion may be formed of the same or different material as the proximal portion. Although a stiffening wire may be placed in the distal portion, if the stiffening wire is not present, the distal portion may be composed of materials that are slightly more stiff than the materials that compose the proximal portion. Optionally, the distal body portion may be reinforced with a metal or polymeric braid or other conventional reinforcing layering.

The distal portion will be sufficiently rigid to permit axial positioning of the distal tip in a ductal orifice with the distal portion extending either partly or wholly into the breast ductal lumen. The distal portion will typically have a hardness in a durometer range at least greater than that of the proximal portion, and thus generally greater than 75D. The hardness of the distal portion thus may be a range from about 70D to about 90D. The proximal portion will be more flexible and less stiff and also less hard than the distal portion. The durometer of the proximal portion outer tubing can be in a range from about 45A to about 100A, and typically about 80A. The inner tubing of the proximal portion can have a durometer in the range from about 50D to about 75D, and typically about 63D. The flexibility of the proximal portion provides the catheter with the advantages that the distal portion (which is stiffer) can be inserted into the breast duct, meanwhile the proximal portion can connect at its hubs with infusion or collection apparatus and not kink during the placement of the distal portion in the breast duct. Additionally, the flexibility of the proximal portion provides the advantage that once the distal portion is placed in the breast duct the catheter will have less tendency to pull out of the duct. The stiffness of the distal portion benefits the procedure by allowing access into the orifice of the duct and the duct itself, an action that requires a probe-like quality of the distal portion and distal tip in order the duct to be accessed successfully.

The catheter body may further comprise other components, such as radiopaque fillers; colorants; reinforcing materials; reinforcement layers, such as braids and helical reinforcement elements; or the like. In particular it would be possible to reinforce the distal portion in order to enhance its duct penetration or probe-like capabilities while optionally limiting its wall thickness and outside diameter so that the catheter can easily access even ducts with small ductal orifices.

The cross-sectional geometry of the distal portion of the catheter body will be smaller than the cross-sectional geometry of the proximal portion. The cross-sectional geometry of the distal portion provides that the distal portion can be inserted into a breast duct orifice and through the orifice into the breast duct lumen. The distal portion of the catheter body has a maximum width in the range from 0.008 inches to 0.050 inches. The distal portion of the catheter body has a generally tubular structure with a diameter in the range from about 0.008 inches to about 0.035 inches. The proximal portion has a cross-sectional geometry which inhibits insertion of the proximal portion into the ductal orifice and the ductal lumen. Thus, the proximal portion of the catheter body has a minimum width in the range from about 0.023 inches to about 0.028 inches. The proximal portion of the catheter body has a generally tubular structure with a diameter in the range from about 0.030 inches to about 0.10 inches. The proximal diameter is greater than the distal diameter by at least about 0.010 inches.

The region between the proximal and distal portions of the catheter body provides for the reduced diameter moving from the proximal to the distal portions. The transition preserves the fluid flow capability and communication in the lumens between the proximal and distal portions and can provide a place to anchor or lodge a wire or stiffening lumen that extends longitudinally in the distal portion. The transition may be stepped, abrupt, or somewhat gradual, provided it allows the proximal portion to retain its function of inhibiting insertion of the catheter into the duct beyond the length of the distal portion.

The ductal access catheter body can comprise at least an infusion lumen and an aspiration lumen each of which has a distal port near a distal end of the distal portion. At least one of the distal aspiration port and the distal infusion portion can be disposed on a side of the distal portion of the catheter body. Thus one port can be a side port and one port can be and end port. The distal aspiration port and the distal infusion port can both be located on the side of the distal portion of the catheter body. Thus, both ports for both lumens can be side ports. The distal aspiration port and the distal infusion port can be axially aligned. Thus, the side ports can be located e.g. opposite each other on the on the distal portion of the catheter body at the longitudinal position. For example, both side ports can be located about 2.5 cm from the distal tip. The distal aspiration port and the distal infusion port can be axially spaced apart. Thus, the side ports can be located at different longitudinal positions on the distal portion, for example one port can be located about 2.0 cm from the distal tip and one port can be located about 2.5 cm from the distal tip. The side ports themselves may be round or oval or any other geometric shape conducive to fluid flow either into the duct or out from the duct. The diameter of the ports can be that diameter which is suitable to achieve a desired flow rate into the duct or aspiration or collection rate out from the duct. Thus, the diameters of the ports can be in a range from about 0.015 inches (0.038 mm) to about 0.022 inches (0.056 mm), most typically in a range from about 0.016 inches (0.041 mm) to about 0.020 inches (0.051 mm). One side port can be larger or smaller than the other, especially where such differential port size provides a desired flow rate into or out from one of the lumens, or an overall lavage efficiency of infusion and aspiration or collection of lavage and ductal fluid.

The catheter body can include an atraumatic distal tip. The tip can be contoured and/or rounded to reduce or eliminate trauma to the duct upon entry through the ductal orifice and penetration into the ductal lumen. The tip may also be fashioned to reduce or eliminate trauma upon withdrawal of the tool from the duct after the lavage procedure is completed. The tip can be composed of a soft polymeric material, e.g. including polyvinyl chloride, polyethers, polyamides, polyethylenes, polyurethanes, copolymers thereof and the like. The tip can have a diameter in the range from about 0.012 inches (0.031 mm) to about 0.020 inches (0.051 mm), more typically a diameter in the range from about 0.014 inches (0.036 mm) to about 0.018 inches (0.046 mm). The length of the tip (extending from the distal end of the distal portion of the catheter) can be in a range from about 0.25 cm to about 2.5 cm, more typically in the range from about 0.50 cm to about 1.8 cm.

The invention also provides a method for lavage of a ductal network in a human breast comprising providing a catheter as any described above for performing the lavage procedure. The distal portion of the catheter is inserted through a ductal orifice and into a distal lumen of the ductal network. A wash fluid is introduced through the infusion lumen into the ductal network. The wash fluid can be, e.g. saline or phosphate buffered saline, or any biocompatible fluid suitable for washing a breast duct lumen. The wash fluid and substances borne by the wash fluid are withdrawn from the ductal network through the aspiration lumen. The various features of the catheters described above can serve to facilitate the practice of the lavage procedure. For example, the narrow distal tip provides the catheter the ability to penetrate the ductal orifice and move the catheter into the ductal lumen for performing the lavage procedure; the larger diameter of the proximal portion inhibits the catheter from passing too deeply into the duct, and stops the penetration of the catheter at the place where the distal portion ends and the proximal portion begins; the atraumatic tip provides the catheter the ability to penetrate the duct without trauma to the tissue walls of the ductal lumen; the stiffening material placed in at least a part of the distal portion of the catheter (e.g. a stiffening wire or a supporting braid or the like) provides the practitioner with stiffness to better control the entry and further penetration of the catheter into the ductal lumen; the ports on the lumens provide the catheter the ability to infuse liquid into the duct from the infusion lumen and the ability to aspirate or collect fluid from the duct into the aspiration lumen; and where the ports are side ports, the presence of side ports may better facilitate the function of the ports for infusing and collecting to and from the duct.

The invention further provides a ductal access system comprising any of the catheters describe herein and instructions for use setting forth a method for lavage of a ductal network in a human breast including introducing a wash fluid through the infusion lumen into the ductal network and withdrawing the wash fluid and substances borne by the wash fluid from the ductal network through the aspiration lumen, e.g. as described for the method above.

EXAMPLES

1. Collecting Cells and Cellular Material Using Single Lumen Ductal Access Device Device as depicted in FIG. 3 was used to access breast ducts of patients A, B, C, D, E, F, G, and H. Before ductal access patient's nipple was cleaned with alcohol, and dekeratinized with cerumetix. An aspiration cup was placed on the nipple and areola and the patient's nipple was aspirated to identify the breast duct and to collect fluid for a comparison with the fluid retrieved from inside the duct. A small quantity of fluid was observed on the nipple surface after aspiration and this fluid was collected with one or more capillary tubes placed in contact with the fluid. The aspiration fluid was preserved in a preservative solution for cells for analysis later.

Ducts that yield fluid were accessed using a dilator that extended from the device depicted in FIG. 3, and once the duct was accessed by the access tube, the dilator was withdrawn. The collection tube was closed, and the system including the infusion tube and manifold were primed with fluid. A total of from 10 ml to about 25 ml of saline infusion fluid was infused into the duct until resistance was felt in the infusion syringe. The assumption made at that point was that the duct was filled with the infusion fluid. The infusion tube was closed and the collection tube opened. The breast was massaged and then squeezed and cloudy fluid was caused to enter the hub and begin to exit the collection tube. To encourage the fluid to exit, the infusion tube was opened and additional infusion fluid was pushed into the hub, causing more cloudy fluid to exit the collection tube. The following fluid amounts refer to the procedure with Patient A. When a volume of about 11.5 ml of fluid was collected, the collection tube was closed and more fluid infused until a resistance was felt in the duct. More fluid was infused to refill the duct. The collection tube was opened, and infusion tube was closed and the breast was massaged and squeezed to encourage more fluid to enter the hub and exit the collection tube. Additionally, the fluid was encouraged to leave the hub with an injection of fluid from the infusion lumen. About 6 ml was collected from the second filling.

The results of the nipple aspiration (NAF), first filling and second filling are reported below for patient A in the Table I. Patient's B, C, and D also have NAF results compared to results using the single lumen catheter, as depicted in Table I. Patients E, F, G and H have yields solely with respect to access and retrieval using the single lumen catheter. Epithelial cell clusters are defined as clusters of cells having greater than 10 epithelial cells per cluster.

TABLE I

| Sample | Collection | Total volume collected | Epithelial Clusters (>10 cells/cluster) |
|---|---|---|---|
| Patient A; duct R2 | NAF (nipple aspiration fluid) | >0.1 ml | 1 epithelial cluster |
| | lavage with single lumen | 17.5 ml | 23 epithelial clusters |
| Patient B; duct L6 | NAF | — | 0 epithelial clusters |
| | lavage with single lumen | — | 31 epithelial clusters |
| Patient C; duct R1 | NAF | 0.2 ml | 0 epithelial clusters |
| | lavage with single lumen | 6 ml | 27 epithelial clusters |
| Patient D; duct on left nipple | NAF | <0.1 ml | 0 epithelial clusters |
| | lavage with single lumen | 7 ml | 101 epithelial clusters |
| Patient E; duct L6 | lavage with single lumen | 11 ml | 3 epithelial clusters |
| Patient F; duct L6 | lavage with single lumen | 10.5 ml | 12 epithelial clusters |
| duct L7 | lavage with single lumen | 7 ml | 7 epithelial clusters |
| duct R1 | lavage with single lumen | 21 ml | 6 epithelial clusters |
| duct R2 | lavage with single lumen | 7 ml | 5 epithelial clusters |
| Patient G; duct L6 | lavage with single lumen | 6 ml | 400 epithielal clusters |
| duct R1 | lavage with single lumen | 8.5 ml | 350 epithelial clusters |
| Patient H; duct L6 | lavage with single lumen | 11 ml | 154 epithelial clusters |
| duct R1 | lavage with single lumen | 7 ml | 131 epithelial clusters |

2. Comparative Study: Pig Pelt Lavage with StopCock Catheter vs. Catheter without StopCocks In order to test the efficiency of the stop cock catheter, a comparison was run comparing the amount of fluid and cells retrieved from a catheter which did not have stop cocks (or on which both stop cocks were kept open during the entire procedure), and a catheter having a stop cock on the inflow lumen and a stop cock on the outflow lumen that are opened and closed alternately during the procedure (in the manner specified below). Two experiments (experiment I and experiment II) were conducted using modified procedures A and B to test modifications to the basic principles of the comparison. The combined results show the increased efficiency of using the stop cock catheter (in the manner described below in the procedure A portion of experiments I & II) to retrieve a larger volume of infused wash fluid and a larger number of ductal cells from the lavaged breast milk duct.

A dual lumen catheter having a support wire is used for the tests. The catheter also has a stopcock on the inflow lumen and a stopcock on the outflow lumen. Frozen pig pelts were purchased from Yosemite Meats, located in Menlo Park, Calif. Procedure A was conducted using the stopcocks controlling the opening and closing of the inflow and outflow lumens at ports located in the stopcocks. Procedure B was conducted with both the inflow and outflow lumens open during the entire procedure. Experiments I and II were conducted as follows:

Procedure A included the following steps:
1. Catheter was inserted into a duct. Both inflow and outflow lumens were primed with wash fluid, and the ports closed (by placing the respective stopcocks in a closed position). The catheter was placed in the duct.
2. The outflow port was opened, and 1 ml of phosphate buffered saline (PBS) was infused into the duct to flush out the outflow lumen. The outflow port was closed.
3. The inflow port was opened and PBS was infused into the duct until resistance to infusion was met. The inflow port was closed.
4. The outflow port was opened. The breast was massaged and squeezed. The outflow fluid was collected.
5. The outflow port remained opened, the inflow port was opened, and 0.5 ml of fluid was infused into the inflow to flush out the outflow lumen. The inflow port was closed and the fluid collected in the collection syringe attached to the outflow lumen.
6. The outflow port was closed and about 1 ml of PBS was infused. The inflow port was closed. The outflow port was opened. The breast was massaged and squeezed, and the fluid collected. Steps 5 and 6 were repeated until about 3 ml of fluid was collected.

Procedure B included the following steps:
1. A dual lumen catheter (with both inflow and outflow ports open) was inserted into the duct.
2. The duct was infused with PBS until the fluid flow into the duct met resistance.
3. The duct was lavaged using massaging and squeezing technique as the fluid was collected in the collection receptacle (located at the end of the outflow lumen).
4. More PBS was infused (each time about 1 ml) and the massaging, squeezing and collecting proceeded. The procedure was repeated until about 3 ml was collected.

Procedure A (one-way flow procedure) included the following steps:
1. Both the inflow and outflow lumens were primed with PBS. The inflow and outflow ports were closed and the catheter inserted into the pig duct to a depth of about 1.5 cm.
2. The outflow port was opened and 1 ml of PBS was infused into the duct to flush out the outflow lumen.

3. The outflow port was closed. The inflow port was opened. Fluid was infused in the inflow port (about 4–5 ml) until resistance was felt. The inflow port was closed.
4. The breast was massaged with both ports closed.
5. The outflow port was opened and the breast squeezed to collect fluid in the collection receptacle until no more fluid comes out.
6. The inflow port was opened and about 0.5 ml of fluid was infused to flush out the outflow lumen.
7. The outflow port was closed and about 1 ml of PBS was infused into the duct in the inflow lumen.
8. The inflow port was closed. The outflow port was opened, and the breast massaged and squeezed to collect the outflow fluid. Steps 6, 7, and 8 were repeated until the collection volume totaled 3 ml.

Procedure B included the following steps:
1. Both the inflow and outflow lumens of a dual lumen catheter were primed with PBS. The catheter tip was inserted into a breast duct of a pig pelt to a depth of about 1.5 cm. About 1 ml of PBS was infused into the duct through the outflow lumen to flush out the outflow lumen.
2. PBS was infused into the inflow port until resistance was felt.
3. The breast was massaged and squeezed as the duct was lavaged with PBS. Fluid flowing to the outflow lumen was collected.
4. More PBS was infused into the duct (each time about 1 ml) and the duct lavaged, (using massaging and squeezing) and the fluid collected in the collection receptacle. The procedure was repeated until about 3 ml of fluid was collected.

The fluid was used to prepare Cytospin® slides by taking 10 ul of collected fluid (plus 90 ul of PBS), using a cytospin machine to place the fluid on a slide.

The slides are air-dried and Diff Quik® stained. The results are shown below in Table II. In all cases 3 ml of fluid was collected, but the infusion volume varied as shown in the table.

TABLE II

| | Procedure A | | Procedure B | | |
| --- | --- | --- | --- | --- | --- |
| nipple | infusion vol | cell density | nipple | infusion vol | cell density |
| experiment I | | | | | |
| X2 | 15 ml | 55% | Z2 | 13 ml | 45% |
| X3 | 18 ml | 65% | X1 | 10 ml | 35% |
| Z3 | 13 ml | 40% | Z1 | 13 ml | 45% |
| Z5 | 12 ml | 55% | | | |
| experiment II | | | | | |
| X1 | 14 ml | 60% | Z1 | 7 ml | 50% |
| X2 | 12 ml | 65% | Z2 | 6 ml | 50% |
| X3 | 13 ml | 65% | Z3 | 6 ml | 40% |
| X4 | 11 ml | 55% | Z4 | 6 ml | 35% |
| average | 13.5 ml | 58% | | 8.7 ml | 43% |

The results indicated a 35% increased cell yield using procedure A over procedure B.

3. Optimal Stop Cock Catheter Usage for Retrieving Cells

A procedure was developed that appeared to optimize the potential yield of cells from the ductal fluid retrieved was a catheter-based lavage procedure of a breast duct. Using pig pelts the following technique resulted in maximized cell yield from a set volume of collected fluid.

1. Inflow and outflow lumens of a dual lumen catheter having stop cocks on both lumens were primed with PBS. The inflow and outflow ports were closed and the catheter inserted into the duct to a depth of about 1.5 cm.
2. The outflow port was opened and 1 ml of PBS was infused into the duct from the outflow lumen to flush out the outflow lumen.
3. The outflow port was closed (using the stopcock) and the inflow port was opened. PBS was infused into the duct until resistance was felt (about 4–5 ml of PBS). The inflow port was closed.
4. The breast was massaged while both the inflow and outflow ports were closed (using the stopcock controls).
5. The outflow port was opened and the breast was massaged and squeezed, and the outflow fluid was collected until no more fluid came out.
6. The outflow port was closed and the inflow opened, and more fluid (about 1 ml) was allowed to infuse into the duct.
7. The inflow port was closed and the outflow port was opened. The breast was massaged and squeezed to collect the fluid.
8. Steps 6 and 7 were repeated until a total of 3 ml of fluid was collected.

This procedure was found to generate the best cell density collect ed in the 3 ml of fluid, and also eliminates one step from previous procedure A.

4. Mannitol Solution Introduced into Breast Ducts of Live Rabbit Results in Increased Ductal Fluid Collection The objective of these experiments was to test the effects of the introduction of a solution containing mannitol on the secretion of fluid from the breast ducts of live rabbits. New Zealand rabbit #3242, female, from Kraelik Farm in California weighing 4.1 kg was used. The rabbit was anesthetized by injection of 200 mg of ketamine and 40 mg of Zylazine. A second injection of 100 mg of ketamine and 20 mg of xylazine was made 2 hours later to maintain the rabbit in a deep plane of anesthesia. The thorax and abdomen of the rabbit was shaved to expose the breasts and nipples.

A single lumen blue color catheter (O.D. 0.23" ID 0.017; O.D. at the tip 0.011"–0.012") was inserted into a duct in each nipple. Three nipples were tested, and 2 ducts per nipple were accessed with a catheter. The nipples were identified A, B, and C.

A duct on nipple A was injected with 0.20 ml of a 12.5% solution of D-Mannitol in $H_2O$ (available from Sigma Chemicals, St. Louis, Mo. cat# M-9546 lot 6710402: $C_6H_{14}O_6$ FW 182.2) with a single catheter. The control duct on nipple A was injected with 0.20 ml of phosphate buffered saline (PBS). A microfuge tube was attached to the end of each catheter to collect out flow liquid. Ten minutes later 0.2 ml of a 12.5% solution of D-Mannitol in $H_2O$ was injected into the first duct and the second duct was injected with 0.20 ml of phosphate buffered saline, for a total volume injected in each duct of 0.40 ml.

A duct on nipple B was injected with 0.5 ml of a 12.5% solution of D-Mannitol in $H_2O$ with a single catheter. The control duct on nipple B was injected with 50 ml of phosphate buffered saline (PBS). A microfuge tube was attached to the end of each catheter to collect out-flow liquid.

A duct on nipple C was injected with 0.7 ml of a 12.5% solution of D-Mannitol in $H_2O$ with a single catheter. The control duct on nipple C was injected with 0.70 ml of phosphate buffered saline (PBS). A microfuge tube was attached to the end of each catheter to collect out flow liquid.

About an hour after the fluid containing mannitol or PBS was injected into the ducts via the catheters, the microfuge tubes were checked for whether any fluid was returned. The results are summarized in the following Table III:

TABLE III

| nipple | duct | solution | recovery | notes |
|--------|------|----------|----------|-------|
| A | A1 | 0.4 ml mannitol 12.5% | 310 ul liquid | fluid was a milky color |
| A | A2 | 0.4 ml PBS | none | — |
| B | B1 | 0.5 ml mannitol 12.5% | 490 ul liquid | fluid was a milky color |
| B | B2 | 0.5 ml PBS | 240 ul liquid | fluid was a milky color |
| C | C1 | 0.7 ml mannitol 12.5% | 280 ul liquid | fluid was a milky color |
| C | C2 | 0.7 ml PBS | none | — |

Davidson green dye (1 ul) was added to each microfuge tube containing fluid for the purpose of taking a picture. The rabbit was euthanized by IV injection of supersaturated KC1. PBS (1.5 ul) was added to each collection. The cells were spun onto Shandon coated slide using megafunnel and cytospin-3 machine (Shandon, Inc. located in Pittsburgh, Pa.) at a speed of 1500/per minute for 15 minutes. The cells were fixed on the slide in 95% ethanol for 10 minutes. The cells were stained using Hematoxylin and Eosin (HE) method of cytology of collected fluid. The results of the cellular analysis are in Table IV:

TABLE IV

| Nipple A/ duct A1 | Nipple B/ duct B1 | Nipple B/ duct B2 | Nipple C/ duct C1 |
|---|---|---|---|
| A few ductal cell clusters and scattered histocytes and apocrine metaplastic cells | A few ductal cell clusters and scattered histocytes and apocrine metaplastic cells | A few ductal cell clusters and scattered histocytes and apocrine metaplastic cells | A few ductal cell clusters and scattered histocytes and apocrine metaplastic cells |

The observations made from this experiment are that fluid can be collected from three out of three ducts injected with mannitol solution; that fluid could be collected from 1 out of 3 ducts injected with PBS solution, and with approximately 50% less volume in the ducts where fluid was collected. There were cells detected from the fluid collected from each duct. The cell morphology looked similar between the mannitol and the PBS injected ducts.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A ductal access device for accessing a breast duct and collecting biological material from within the duct said device comprising:
  an elongated member comprising an outer diameter sized for positioning within the breast duct and an internal lumen for infusing fluid into the breast duct and retrieving the biological material from within the breast duct; and
  a body for infusing fluid into said elongated member, said body comprising four openings in communication with said internal lumen of said elongated member.

2. The ductal access device of claim 1 wherein one of said openings includes a fluid tight seal.

3. The ductal access device of claim 2 wherein said fluid tight seal includes an opening for receiving a stiffening member.

4. The ductal access device of claim 3 wherein said stiffening member includes a tapered dilator.

5. The ductal access device of claim 1 wherein one of said openings includes a fluid infusion port and another of said openings includes a fluid collection port.

6. The ductal access device of claim 5 further comprising a compressible lumen extending from said fluid infusion port for connecting said fluid infusion port to a fluid containing device, wherein said compressible lumen can be used to control fluid flow to the infusion port.

7. The ductal access device of claim 5 further comprising a compressible lumen extending from said fluid collection port for connecting said fluid collection port to a fluid collection device, wherein said compressible lumen can be used to control fluid flow from said fluid collection port.

8. The ductal access device of claim 5 wherein said infusion and collection ports each include a longitudinal axis that extends into said body at an angle to a longitudinal axis of said body.

9. The ductal access device of claim 5 wherein said infusion port and said collection port are spaced from each other along a length of said body.

10. The ductal access device of claim 5 wherein said infusion port is proximate said elongated member relative to said collection port.

11. The ductal access device of claim 1 wherein one of said openings includes a port positioned at a distal end of said body and proximate an end of said elongated member.

12. The ductal access device of claim 1 wherein said elongated member includes only one lumen.

13. The ductal access device of claim 1 further comprising an anchor attached to one of said body or said elongated member for securing the ductal access device relative to a patient.

14. The ductal access device of claim 1 wherein said body includes an outer diameter that is greater than an outer diameter of said elongated member.

15. The ductal access device of claim 1 wherein said elongated member includes an atraumatic distal tip.

16. The ductal access device of claim 1 wherein said body has a volume of from about 0.01 ml. to about 1.0 ml.

17. A device for accessing a breast duct and performing ductal lavage, said device comprising:
  a fluid hub comprising a proximal end, a distal end and at least three openings; and
  an elongated member for positioning within the breast duct comprising an internal lumen for infusing fluid into the breast duct and retrieving fluid from within the duct, said lumen being in communication with said openings of said fluid hub, and a length sized such that a distal end of said elongated member is positioned distal a ductal sphincter and proximal a portion of the breast duct to be lavaged when said distal end of said hub is proximate a ductal opening on a nipple surface.

18. The device of claim 17 wherein said at least three openings include a fluid infusion port and a fluid collection port.

19. The device of claim 18 further comprising a compressible lumen extending from said fluid infusion port for connecting said fluid infusion port to a fluid containing device, wherein said compressible lumen can be used to control fluid flow to the infusion port.

20. The device of claim 18 further comprising a compressible lumen extending from said fluid collection port for connecting said fluid collection port to a fluid collection device, wherein said compressible lumen can be used to control fluid flow from said fluid collection port.

21. The device of claim 18 wherein said infusion port and said collection port are spaced from each other along a length of said hub.

22. The device of claim 21 wherein said infusion port is positioned proximate said elongated member relative to said collection port.

23. The device of claim 17 wherein said elongated member includes only one lumen.

24. The device of claim 17 further comprising an anchor attached to one of said hub or said elongated member for securing said device relative to a patient.

25. The device of claim 17 wherein said hub includes an outer diameter that is greater than an outer diameter of said elongated member.

26. The device of claim 17 wherein said elongated member includes an atraumatic distal tip.

27. The device of claim 17 wherein said hub has an inner volume of from about 0.01 ml. to about 1.0 ml.

28. The device of claim 17 wherein said at least three openings include four openings.

29. The device of claim 28 wherein one of said openings includes a fluid tight seal.

30. The device of claim 29 wherein said fluid tight seal includes an opening for receiving a stiffening member.

31. The device of claim 30 wherein said stiffening member includes a tapered dilator.

32. A device for accessing a breast duct having multiple branches and performing ductal lavage within said duct, said device comprising:
an elongated member comprising an outer diameter sized for positioning within the breast duct and having an internal lumen for infusing a fluid into the breast duct and retrieving cellular material from within the branches; and
a body for infusing fluid into said elongated member, said body comprising at least three openings for communicating with said internal lumen and dimensions such that said elongated member remains within the breast duct and capable of retrieving the cellular material from within the branches of the duct being lavaged after said elongated member has been positioned within said duct and said body is free of external support from a practitioner or assistant.

33. The device of claim 32 wherein one of said openings is at a distal end of said body proximate said elongated member.

34. The device of claim 32 wherein one of said openings includes a fluid infusion port and another of said openings includes a fluid collection port.

35. The device of claim 34 further comprising a compressible lumen extending from said fluid infusion port for connecting said fluid infusion port to a fluid containing device, wherein said compressible lumen can be used to control fluid flow to the infusion port.

36. The device of claim 34 further comprising a compressible lumen extending from said fluid collection port for connecting said fluid collection port to a fluid collection device, wherein said compressible lumen can be used to control fluid flow from said fluid collection port.

37. The device of claim 34 wherein said infusion and collection ports each include a longitudinal axis that extends into said body at an angle to a longitudinal axis of said body.

38. The device of claim 34 said infusion port and said collection port are spaced from each other along a length of said body.

39. The device of claim 34 wherein said infusion port is proximate said elongated member relative to said collection port.

40. The device of claim 34 wherein said elongated member includes only one lumen.

41. The device of claim 32 wherein said elongated member includes only one lumen.

42. The device of claim 32 further comprising an anchor attached to one of said body or said elongated member for securing the device relative to a patient.

43. The device of claim 32 wherein said body includes an outer diameter that is greater than an outer diameter of said elongated member.

44. The device of claim 32 wherein said elongated member includes an atraumatic distal tip.

45. The device of claim 32 wherein said body has an inner volume of from about 0.01 ml. to about 1.0 ml.

46. The device of claim 32 wherein said at least three openings includes four openings.

47. The device of claim 32 wherein one of said openings includes a fluid-tight seal.

48. The device of claim 47 wherein said fluid tight seal includes an opening for receiving a stiffening member.

49. The device of claim 48 wherein said stiffening member includes a tapered dilator.

50. A ductal access device for accessing a breast duct and collecting biological material from within the duct, said device comprising:
an elongated member comprising an outer diameter sized for positioning within the breast duct and having an internal lumen for retrieving the biological material from within the duct;
a body for infusing fluid into said elongated member, said body comprising at least three openings in communication with said internal lumen of said elongated member; and
an anchor operatively connected to said elongated member and said body for stabilizing the position of the elongated member within the duct and the body relative to a breast in which the elongated member extends.

51. The ductal access device of claim 50 wherein said anchor includes a securing member configured for being attached to a portion of a body of a patient.

52. The ductal access device of claim 51 wherein the securing member includes a tether having an adhesive for contacting and adhering to the portion of the body of the patient.

53. The ductal access device of claim 50 wherein said anchor extends from one of said body and said elongated member.

54. The ductal access device of claim 50 wherein one of said openings includes a fluid tight seal.

55. The ductal access device of claim 54 wherein said fluid tight seal includes an opening for receiving a dilator.

56. The ductal access device of claim 50 wherein one of said openings includes a fluid infusion port and another of said openings includes a fluid collection port.

57. The ductal access device of claim 56 wherein said infusion port and said collection port are spaced from each other along a length of said body.

58. The ductal access device of claim 57 wherein said infusion port is positioned proximate said elongated member relative to said collection port.

59. The ductal access device of claim 50 wherein said elongated member includes only one lumen.

60. The ductal access device of claim 50 wherein said body includes an outer diameter that is greater than an outer diameter of said elongated member.

61. The ductal access device of claim 50 wherein said elongated member includes an atraumatic distal tip.

62. The ductal access device of claim 50 wherein said body has a volume of from about 0.01 ml. to about 1.0 ml.

63. A ductal access device for accessing a breast duct and collecting cellular material from within the duct, said device comprising:
   a single elongated member comprising an outer diameter sized for positioning within the breast duct and an inner diameter for introducing fluid into the duct and receiving cellular material from within the duct; and
   a manifold hub for receiving cellular material from the breast duct carried by the elongated member, said manifold hub comprising at least three openings in communication with said elongated member and an inner diameter that is greater than the inner diameter of said elongated member.

64. The ductal access device of claim 63 wherein said inner diameter of said elongated member is from about 0.007 inch to about 0.047 inch.

65. The ductal access device of claim 63 wherein an outer diameter of said hub is greater than the outer diameter of said elongated member.

66. The ductal access device of claim 65 wherein the outer diameter of said elongated member is from about 0.010 inch to about 0.50 inch.

67. The ductal access device of claim 63 wherein said hub has an inner volume of from about 0.01 ml. to about 1.0 ml.

68. The ductal access device of claim 63 wherein said at least three openings include a fluid infusion port and a fluid collection port.

69. The ductal access device of claim 68 further comprising a compressible lumen extending from said fluid infusion port for connecting said fluid infusion port to a fluid containing device, wherein said compressible lumen can be used to control fluid flow to the infusion port.

70. The ductal access device of claim 68 further comprising a compressible lumen extending from said fluid collection port for connecting said fluid collection port to a fluid collection device, wherein said compressible lumen can be used to control fluid flow from said fluid collection port.

71. The ductal access device of claim 68 wherein said infusion port is positioned proximate said elongated member relative to said collection port.

72. The ductal access device of claim 63 further comprising an anchor attached to one of said hub or said elongated member for securing said device relative to a patient.

73. The ductal access device of claim 63 wherein said at least three openings include four openings.

74. The ductal access device of claim 73 wherein one of said four openings includes a fluid tight seal.

75. The ductal access device of claim 74 wherein said fluid tight seal includes an opening for receiving a stiffening member.

76. The ductal access device of claim 75 wherein said stiffening member includes a tapered dilator.

77. The ductal access device of claim 63 wherein said elongated member includes only one lumen.

78. The ductal access device of claim 63 wherein said elongated member includes an atraumatic distal tip.

79. A ductal access device for accessing a breast duct and collecting cellular material from within the duct, said device comprising:
   an elongated member comprising an outer diameter sized for positioning within the breast duct and an internal lumen;
   a manifold hub comprising a plurality of openings in communication with said internal lumen; and
   a stiffening member extending within said internal lumen and past a distal end of said elongated member as said ductal access device is introduced into the breast duct.

80. The ductal access device of claim 79 wherein said stiffening member includes a dilator.

81. The ductal access device of claim 80 wherein said dilator is a tapered dilator.

82. The ductal access device of claim 80 wherein said dilator has an outer diameter at a point along its length of about 0.024 inches or less.

83. The ductal access device of claim 79 wherein said stiffening member has a first diameter at a distal end thereof and a second, larger diameter at a point proximate a distal end of said elongated member.

84. The ductal access device of claim 83 wherein said distal end of said elongated member includes an atraumatic tip.

85. The ductal access device of claim 79 further comprising an anchor for securing said elongated member and said hub relative to a portion of a body of a patient.

86. The ductal access device of claim 79 wherein said plurality of openings includes at least three openings.

87. The ductal access device of claim 86 wherein a first one of said openings includes a fluid infusion port, a second one of said openings includes a fluid collection port and a third one of said openings includes an access port positioned at a distal end of said hub proximate said elongated member.

88. The ductal access device of claim 86 further including a fourth opening at a proximal end of said hub.

89. The ductal access device of claim 88 wherein said fourth opening includes a fluid-tight seal for receiving said stiffening member.

90. The ductal access device of claim 79 wherein said elongated member includes only one lumen.

91. The ductal access device of claim 79 wherein said hub has a volume of from about 0.01 ml. to about 1.0 ml.

92. The ductal access device of claim 79 wherein said hub includes an outer diameter that is greater than an outer diameter of said elongated member.

93. A ductal access device comprising:
   a hub comprising an internal elongate manifold and at least three openings; and
   an elongated member comprising a distal end including an atraumatic tip, a proximal end, a single lumen in communication with said hub openings and extending between said distal and proximal ends, and dimensions which permit introduction of the distal end through a ductal orifice and positioning a distal end of said elongated member distal to a ductal sphincter and proximal a first bifurcation in a human breast duct.

94. The ductal access device of claim 93 further comprising a dilator for extending from said atraumatic tip as said elongated member is introduced into a breast duct.

95. The ductal access device of claim 94 wherein said dilator has a first diameter at a distal end thereof and a second, larger diameter at a point proximate said atraumatic tip of said elongated member.

96. The ductal access device of claim 93 further comprising an anchor for securing said elongated member and said hub relative to a portion of a body of a patient.

97. The ductal access device of claim 93 wherein said at least three openings includes a fluid infusion port, a fluid collection port and an access port positioned at a distal end of said hub proximate said elongated member.

98. The ductal access device of claim 97 wherein said at least three openings further include a fourth opening.

99. The ductal access device of claim 98 wherein said fourth opening includes a fluid-tight seal at a proximal end of said hub.

100. The ductal access device of claim 93 wherein said hub includes an outer diameter that is greater than an outer diameter of said elongated member.

101. The ductal access device of claim 93 wherein said hub has a volume of from about 0.01 ml. to about 1.0 ml.

* * * * *